(12) United States Patent
Mayfield

(10) Patent No.: US 6,294,653 B1
(45) Date of Patent: Sep. 25, 2001

(54) RNA BINDING PROTEIN AND BINDING SITE USEFUL FOR EXPRESSION OF RECOMBINANT MOLECULES

(75) Inventor: Stephen Mayfield, Cardiff, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/613,182

(22) Filed: Jul. 10, 2000

Related U.S. Application Data

(62) Division of application No. 09/341,550, filed on Jul. 13, 1999, now Pat. No. 6,156,517.
(60) Provisional application No. 60/035,955, filed on Jan. 17, 1997, and provisional application No. 60/069,400, filed on Dec. 12, 1997.

(51) Int. Cl.[7] .................................................. C07K 14/415
(52) U.S. Cl. ............................................................. 530/350
(58) Field of Search .............................................. 530/350

(56) References Cited

PUBLICATIONS

Danon et al., EMBO J., vol. 10, 1991, pp. 3993–4001.*
Danon et al., EMBO J., vol. 13, 1994, pp. 2227–2235.*
Yohn, Altered mRNA binding activity and decreased translation initiation in a nuclear mutant lacking translation of the chloroplast psbA, mRN 1996, *Mol. Cell. Biol.*, 16(7):3560–3566.

* cited by examiner

*Primary Examiner*—James Ketter
(74) *Attorney, Agent, or Firm*—Emily Holmes; Thomas Fitting

(57) ABSTRACT

The present invention relates to recombinant protein disulfide isomerase, RB60, that functions as a translational regulator of the binding of a translational activator protein, RB47, to its binding site for the activation of translation. The recombinant RB60 protein is useful in a gene expression system in eukaryotic and prokaryotic cells, preferably plant cells and intact plants.

1 Claim, 17 Drawing Sheets

```
  1 GAATTCGGCGCCGCTCCGTGGTTGGTCCTC ATG GTG TCT TTT TGA AGAGGACCTGAGCCTTTCACCCAATATA  74
                                   M   V   S   F   *                                 1

75 TCAAAAACCCGGGCAACCGGCCAAAAAATTGCAAAGCCTCTCGTAGGCACAAAGACCTATTCTAGCCATCAACTTT    154

155 GTATCCGACGCTGCCGTTAGCTGCGCGTCTTGAAGTCAAGC ATG GCG ACT ACT GAG TCC TCG GCC CCG   223
                                              M   A   T   T   E   S   S   A   P       9

224 GCG GCC ACC CAG CCG GCC AGC CCG CTG GCG AAC TCG TCG CTG TAC GTC GGT GAC         283
 10  A   A   T   Q   P   A   S   P   L   A   N   S   S   L   Y   V   G   D          29

284 CTG GAG AAG GAT GTC ACC GAG GCC CAG CTG TTC GAG CTC TTC TCG GTT GGC CCT GTG     343
 30  L   E   K   D   V   T   E   A   Q   L   F   E   L   F   S   V   G   P   V       49

344 GCC TCC ATT CGC GTG TGC CGC GAT GCC GTC ACG CGC CTG GGC TAC GCC TAC GTC         403
 50  A   S   I   R   V   C   R   D   A   V   T   R   L   G   Y   A   Y   V          69

404 AAC TAC AAC AGC GCT CTG GAC CCC CAG GCT GCT GAC CGC ATG GAG ACC CTG AAC TAC     463
 70  N   Y   N   S   A   L   D   P   Q   A   A   D   R   M   E   T   L   N   Y       89

464 CAT GTC GTG AAC GGC AAG CCT ATG ATG CGC ATC ATG TGG TCG CAC CGC GAC CCT TCG GCC CGC 523
 90  H   V   V   N   G   K   P   M   M   R   I   M   W   S   H   R   D   P   S   A   R  109

524 AAG TCG GGC GTC GGC TTC TCG GCC AAC ATC TTC ATC AAG AAC CTG GAC AAG ACC ATC GAC AAG GCC 583
110  K   S   G   V   G   F   S   A   N   I   F   I   K   N   L   D   K   T   I   D   K   A  129

584 CTG CAC GAC ACC TTC GGC TAC GGC TTC GTG CAC TTC GAG ATT CTG TCC TGC AAG GTT GCC GCT GAC GCC 643
130  L   H   D   T   F   G   Y   G   F   V   H   F   E   I   L   S   C   K   V   A   T   D   A  149

644 AAC GGC GTG TCG AAG CAG AAC CAG GGC TAC AAG AAG ATT GAG GGC AAG ATC GTG TAC GTG GCC GCT CGC 703
150  N   G   V   S   K   Q   N   Q   G   Y   K   K   I   E   G   K   I   V   Y   V   A   A   R  169

704 GCC ATT CAG ACC GTC AAC CAG AAG GGC AAG ATC GAG GGC AAG ATC GTG TAC GTG GCC CCC TTC         763
170  A   I   Q   T   V   N   Q   K   G   K   I   E   G   K   I   V   Y   V   A   P   F          189
```

FIG. 1A

```
 764 CAG AAG CGC GCT GAC CGC CCC AGG GCA ACG TTG TAC ACC AAC GTG TTC GTC AAG AAC  823
 190  Q   K   R   A   D   R   P   R   A   T   L   Y   T   N   V   F   V   K   N   209

824 TTG CCG GCC GAC ATC GGC GAC CGC GAG CTG GGC ATG AAG ACC GCC CAC GGC GAG ATC  883
 210  L   P   A   D   I   G   D   R   E   L   G   M   K   T   A   H   G   E   I   229

884 ACC AGC GCG GTG GTC ATG AAG GAC GAG CTG AAG AGC GGC AAG TTC GGC TTC ATC AAC  943
 230  T   S   A   V   V   M   K   D   E   L   K   S   G   K   F   G   F   I   N   249

944 TTC AAG GAC GCC GAG CTG TAC TGC GTG GGC GAG TAC CTG AAC GAG CGC GAG ATG AGC 1003
 250  F   K   D   A   E   L   Y   C   V   G   E   Y   L   N   E   R   E   M   S   269

1004 GGC AAG ACC CTG TAC GCC GAG CGC CAG GCC AAG CGC GAG GCG ATG CGC CTG CGC 1063
 270  G   K   T   L   Y   A   E   R   Q   A   K   R   E   A   M   R   L   R   289

1064 CAG AAG GAG GAG AGC AAG GCC CGC GAG CAG TAC CTG AAG AAG ACC CAG TAC CTG TAC 1123
 290  Q   K   E   E   S   K   A   R   E   Q   Y   L   K   K   T   Q   Y   L   Y   309

1124 GTC AAG AAC CTG TCC GAC GAG ATC ACC TCG TGC AAG GTC ATG CGT TAC GAC GAC CTG 1183
 310  V   K   N   L   S   D   E   I   T   S   C   K   V   M   K   R   Y   D   D   L   329

1184 TCT GGC ATC ACC TTC GAC GAG AAG ATG AAG GGC GAC AAG TCC AAG GCC AAG GGC TTC 1243
 330  S   G   I   T   F   D   E   K   M   K   G   D   K   S   K   G   F   349

1244 GGC TTC TGC TTC ACC AGC TCG GAC GAG GTC CAC GAG GAC CAC GAC GTG ACC CCG CTG ACC GCC 1303
 350  G   F   C   F   T   S   S   D   E   V   H   E   D   H   D   V   T   P   V   A   369

1304 GGC AAG ATG GTC AAG TTC GGC AAG TAC GTG TAC GAC GAC CAC CAC ACC AAG GCC AAG GCC ATG 1363
 370  G   K   M   V   K   F   G   K   Y   V   Y   D   D   H   H   T   R   K   D   V   M   389

1364 CGT GCC ACC CAG CTG GAG GCC AAC ATG CAG GCG CGC ATG GGC ATG AAC CGC CGC 1423
 390  R   A   T   Q   L   E   A   N   M   Q   A   R   M   G   M   N   Q   A   M   S   R   409
```

FIG. 1B

```
1424 CCG CCG AAC CCG ATG GCC GGC ATG AGC CCC TAC CCC GGC GCC ATG CCG TTC TTC GCT CCC 1483
410   P   P   N   P   M   A   G   M   S   P   Y   P   G   A   M   P   F   F   A   P   429

1484 GGC CCC GGC GGC ATG GCT GCT GCT GGC ATG CCG CGC GCT ATG ATG TAC CCG TTC CCC ATG 1543
430   G   P   G   G   M   A   A   A   G   M   P   R   A   M   M   Y   P   F   P   M   449

1544 CCG CCG CGC GGC CGC ATG CCT GGC GGC CCC ATG GGC CGC CCC ATG ATG CCG CCC CAG ATG 1603
450   P   P   R   G   R   M   P   G   G   P   M   G   R   P   M   M   P   P   Q   M   469

1604 ATG ATG GGT GGC ATG ATG GGC CGC CCC CCC ATG GGC CGC CGT GGC CGC CCC CAG CGC 1663
470   M   M   G   G   M   M   G   R   P   P   M   G   R   R   G   R   P   Q   R   489

1664 GGC CCC TCC GGC CGC CAG GGC AAC AAC GCC CCT GGG CAG CAG CCC AAG CCC 1723
490   G   P   S   G   R   Q   G   N   N   A   P   G   Q   Q   P   K   P   509

1724 GCC GCT GAG CCC GCC GCC GCC CCC GCT GCC GCG CCT GCC GCC 1783
510   A   A   E   P   A   A   A   P   A   A   A   P   A   A   529

1784 GCG GCG GCG GAG GCC CCC CAG CAG CAG CCG CTG ACC GCC CTG TAC CCG CAG CTG GCC 1843
530   A   A   A   E   A   P   Q   Q   Q   P   L   T   A   L   Y   P   Q   L   A   549

1844 GCC GCG GCG GAG CCG GAG CAG CAG AAG ATG ATC ACC GGG ATG CTG GAG ATG CTG CTG GTG GCG 1903
550   A   A   A   E   P   E   Q   Q   K   M   I   T   G   M   L   E   M   L   L   V   A   569

1904 CTG CAG CCC GAC CTT GCT GGT AAG ATC ACC CAC GAG ATG GAC AAC GCC GAG 1963
570   L   Q   P   D   L   A   G   K   I   T   H   E   M   D   N   A   E   589

1964 CTT CTG ATG CTT CTG GAG TCG CAC GAG GCG CTG GTG TCC AAG GTG GAC GAG GCC ATC GCT 2023
590   L   L   M   L   L   E   S   H   E   A   L   V   S   K   V   D   E   A   I   A   609

2024 GTG CTC AAG CAG CAC AAC GTG ATT GCC GAG GAG AAC AAG GCT TAA AGCGCCTGCACGCTTGTGCG 2088
610   V   L   K   Q   H   N   V   I   A   E   E   N   K   A   *                         624
```

FIG. 1C

```
2089  GGCTGGTGGCGGCCGCGCCGCCGCTGCTTGGCCGCCAGC ATG GGC GCG GCG GAC GCG GTG TGG  2159
                                                   M   G   A   A   D   A   V   W    8

2160  GAG CAG TGC TTG CTG CTT CTG GCC GCC GTG AAG CCG CGC CGA ACT GGG GCG GAC GCG AGG  2219
   9   E   Q   C   L   L   L   L   A   A   V   K   P   R   R   T   G   A   D   G   R   28

2220  CTG GCG TTG ACG CCG GCG CGC CAC AAC ACA AAG TTG GTG GCG TGA AAGTCTCGGGCGTGCTCCG  2284
  29   L   A   L   T   P   A   R   H   N   T   K   L   V   A   *                      43

2285  GACGGTTGTAAGTTTAAGAACTGGCTTTTGCCCGGTTGCCGCCCAAAGGCGGAACGGCGGTCTTTCAGGCCAATCA     2364

2365  CATCCGGCTGAAAAATTCTTACCAAGCCAACCCCCTGCACCCAAAGAACCCAAATTTCGGGTTCCGAAAGAACACTCCCCCTTTTT  2444

2445  CCGGCAACGCGTTCTTTCAAGCCAATCACTTCCGGTTGGAAGAAA ATG TTA CCC GGA AAA GGC GGG AAG  2516
                                                     M   L   P   G   K   G   G   K    8

2517  CCC CCT GCA CCC GGA CAA GTT ATT CGG GGT TTC GCC AAT GAG CAA AAT GCG TTC GGG CTG  2576
   9   P   P   A   P   G   Q   V   I   R   G   F   A   N   E   Q   N   A   F   G   L   28

2577  TTG GCC GTA TCG CGA ACG CTG TCG GGG TGT CAG GCG CCA GAA GGA AGG ATG ACG TTT TGG  2636
  29   L   A   V   S   R   T   L   S   G   C   Q   A   P   E   G   R   M   T   F   W   48

2637  TGA AGGGGTGCAAACTGAGCACGAGTTTTGGCAATAGACGTGAGACAAAGTCCAGTGCGGGGTGAGGCGGATAGCGGA  2715
  49   *                                                                               49

2716  ATCAAGCGTGGGGAGTCCCTGGCGAGACGAGAGACGCTTCTGTGTTTTGCTGAGCCCTTTG ATG GCA CAA TCG CAC  2790
   1                                                                 M   A   Q   S   H    5

2791  TGT TTT GAG CAG GCG ACT GTA AAG TGC CCG ACG CTA AAA AAG CGG CCG CGA ATT CC       2846
   6   C   F   E   Q   A   T   V   K   C   P   T   L   K   K   R   P   R   I           23
```

FIG. 1D

MNRWNLLALTLGLLLVAAPFTKHQFAHASDEYEDDEEDDAPAAP

KDDDVDVTVTVKNWDETVKKSKFALVEFYAPWCGHCKTLKPEYAKAATALKAAAPDA

LIAKVDATQEESLAQKFGVQGYPTLKWFVDGELASDYNGPRDADGIVGWVKKTGPPA

VTVEDADKLKSLEADAEVVVVGYFKALEGEIYDTFKSYAAKTEDVVFVQTTSADVAKA

AGLDAVDTVSVKNFAGEDRATAVLATDIDTDSLIAFVKSEKMPPTIEFNQKNSDKIF

NSGINKQLILWTTADDLKADAEIMTVFREASKKFKGQLVFVTVNNEGDGADPVTNFFG

LKGATSPVLLGFFMEKNKKFRMEGEFTADNVAKFAESVVDGTAQAVLKSEAIPEDPYE

DGVYKIVGKTVESVVLDETKDVLLEVYAPWCGHCKKLEPIYKKLAKRFKKVDSVIIAK

MDGTENEHPEIEVKGFPTILFYPAGSDRTPIVFEGGDRSLKSLTKFIKTNAKIPYELP
KKGSDGDEGTSDDKDKPASDKDEL

```
  1 gagtacgttt acgccatgaa ccgttggaac cttcttgccc ttacccctggg gctgctgctg
 61 gtggcagcgc ccttcaccaa gcaccagttt gctcatgctt ccgatgagta tgaggacgac
121 gaggaggacg atgccccccgc cgcccctaag cgtcgacgacg tcgacgttac tgtggtgacc
181 gtcaagaaact gggatgagac cgtcaagaag tccaagttcg cgcttgtgga gttctacgct
241 ccttggtgcg gccactgcaa gacccctcaag cctgagtacg ctaaggctgc caccgccctg
301 aaggctgctg ctcccgatgc cctttatcgcc gggctaccccc aaggtcgacg ccacccagga ggagtccctg
361 gcccagaagt tcggcgtgca gggctaccgca acccctcaagt ggttcgttga tggcgagctg
421 gcttctgact acaacggccc ccgcgacgct gatggcattg ttggctgggt gaagaagaag
481 actggccccc ccgccgtgac cgttgaggac gccgacaagc tgaagtccct ggaggcggac
541 gctgaggtcg ttgtcgtcgg ctacttcaag gcccctggagg bcgagatcta cgacaccttc
601 aagtcctacg ccgccaagac cgaggacgtg gtgttcgtgc agaccaccag cgccgacgtc
```

```
 661 gccaaggccg ccggcctgga cgccgtggac accgtgtccg tggtcaagaa cttcgccggt
 721 gaggaccgcg ccaccgccgt cctggccacg cctggccaca ctgactccct gaccgcgttc
 781 gtcaagtcgg agaagatgcc ccccaccatt gagttcaacc agaagaactc tgacaagatc
 841 ttcaacagcg gcatcaacaa gcagctgatt ctgtggacca ccgccgacga cctgaaggcc
 901 gacgccgaga tcatgactgt gttccgcgag agttcaaggg gccagcaaga agttcaaggg ccagctggtg
 961 ttcgtgaccg tcaacaacga gggcgacgcg gtcaccaactt cttcggcctc
1021 aagggcgcca cctcgcctgt gctgctgggc ttcttcatgg agaagaacaa gaagttccgc
1081 atggaggcgg agttcacggc tgacaacgtg gctaagttcg ccgagagcgt ggtggacggc
1141 accgcgcagg ccgtgctcaa gtcggaggcc atccccgagg accctatga ggatggcgtc
1201 tacaagattg tgggcaagac cgtggagtct gtggtttctgg acgagaccaa ggacgtgctg
1261 ctgaggttgt acgccccctg gtgcgggcca tgcaagaagc tggagcccat ctacaagaag
1321 ctggccaagc gctttaagaa gggctggatt tgacaacatcc ccaagatgga tggcactgag
1381 aacgagcacc ccgagatcga cggtcaaggc gttcccatacca tcctgttcta tccccgccggc
1441 agcgaccgca cccaacgcca gatcccgtac ggcgaccgct cgctcaagtc cctgaccaag
1501 ttcatcaaga cccaagccaa ggacagccc gagctgcgcc agaaggccct cgacggcgac
1561 gagggcacct cggatcgacac ggacagccag gcgtccgcga gaagggcgga gtaagcggct
1621 atctgaacta cccccaggtt ggagcagcag caacggcgga tgcttggggg cactgtgcat
1681 ggatgggagt taaggaggag ggctgttgct ggagaggata cgggccggg ccttggagcat
1741 ccggcagcgc gcggatcctc gtgatccggt ggcagcagcag ctggccaaag tccacagccc
1801 gctggccgag aagacgagac ccccaggttt ggagagagtc cttggacatgg gcgcgggcgg
1861 agagatgaga catgaaggac gcgttacggg ctggcatgcc tggcaagatg agcctaggggc
1921 cttgctagga gaactagga taagcagca ctgtgtattc catgtgtgagg ctgtcgcctt
1981 agtttttag gcctccggag cattgaactc tttgcaagtc tggctagctaag cttggaagtg
2041 cgtactcctc aagcagctag cattgagcat actagtatgc agcgccttg agatgaacaa
2101 gtgccccgac gagccaagag cttgaggcaa cctcctctag aagccggag tggatgatt
2161 ggttccgaag catgaagagct gctgttgagg tctgtttgaag agcaagcgga ttgatgcgt
2221 ggccgcgtga gacgcttagg tgtccggatg gggatttgcc ggggatgatg cgccccggcac
2281 cagcggatcg agctagcgca agctagcgca ggattttgcga gcagcggccag cgcagcaggcg
2341 ggagccaagg cggagtgcat gcgaggaaaa cagtgtgcgg tcgcggcgtg cgatcagggga
2401 cgccttgcgc aaa                                      gctgcaagaa
```

CTT CTT TAC GGT AAC AAC ATC ATT ACA GGT GCT GTA ATC CCA ACT TCT AAC GCA ATC GGT
Leu Leu Tyr Gly Asn Asn Ile Ile Thr Gly Ala Val Ile Pro Thr Ser Asn Ala Ile Gly 90
                                    Ser         Ile                 Ala
                                        .300                            .250

CTT CAC TTC TAC CCA ATT TGG GAA GCT TCT CTA GAC TCT GCT GAG TGG TTA TAC AAC GGT GGT
Leu His Phe Tyr Pro Ile Trp Glu Ala Ser Leu Asp Ser Ala Glu Trp Leu Tyr Asn Gly Gly 110
                                            Val
                                    .350

CCT TAC CAA CTT ATC GTT TGT CAC TTC CTA GGT GTA TAC TGC TAC ATG GGT CGT GAG
Pro Tyr Gln Leu Ile Val Cys His Phe Leu Leu Gly Val Tyr Cys Tyr Met Gly Arg Glu 130
        Glu                         Leu                         Ala
                    .400                                                    .450

TGG GAA TTA TCT TTC CGT ATG GGT TTA GTT TAC CCT ATC TGG ATC CCA TAC TCA GCT CCA
Trp Glu Leu Ser Phe Arg Met Gly Leu Val Tyr Pro Ile Trp Ile Pro Tyr Ser Ala Pro 150
                                            Ile

GTA GCT GCA GCT TCA GCT ALA TCT GTA TTC ATC GGC CAA GGT TCA TTC TCT GAC
Val Ala Ala Ala Ser Ala Ala Ser Val Phe Ile Gly Gln Gly Ser Phe Ser Asp 170
                    Thr
                                                        .500

GGT ATG CCT TTA GGT ATC TCT GGT ACT TTC AAC TTC ATG GTA TTC CAA GCA GAA CAC
Gly Met Pro Leu Gly Ile Ser Gly Thr Phe Asn Phe Met Ile Val Phe Gln Ala Glu His 190
                            .600
                                                .550

AAC ATC CTT ATG CAC CCA TTC CAC ATG TTA GGT GTT GCT GGT GTA TTC GGT GGT TCA TTA
Asn Ile Leu Met His Pro Phe His Met Leu Gly Val Ala Gly Val Phe Gly Gly Ser Leu 210

TTC TCA GCT ATG CAC GGT TCT TTA GTT ACT TCA TCT TTA ATC CGT GAA ACA ACT GAA AAC
Phe Ser Ala Met His Gly Ser Leu Val Thr Ser Ser Leu Ile Arg Glu Thr Thr Glu Asn 230
            850

FIG. 3B

```
                                                                                         .750
GAA TCA GCT AAC GAA GGT TAC CGT TTC GGT CAA GAA GAA ACT TAC AAC ATT GTA GCT
Glu Ser Ala Asn Glu Gly Tyr Arg Phe Gly Gln Glu Glu Thr Tyr Asn Ile Val Ala  250

.800
GCT CAT]GGT TAC TTT GGT CGT CTA ATC TTC CAA TAC GCT TCT TTC AAC AAC TCT CGT TCA
Ala His]Gly Tyr Phe Gly Arg Leu Ile Phe Gln Tyr Ala Ser Phe Asn Asn Ser Arg Ser  270

.850
TTA CAC TTC TTC TTA GCT GCT TGG CCG GTA ATC GGT ATT TGG TTC ACT GCT TTA GGT TTA
Leu His Phe Phe Leu Ala Ala Trp Pro Val Ile Gly Ile Trp Phe Thr Ala Leu Gly Leu  290
                                    Val                                       Ile

.900
TCA ACT ATG GCA TTC AAC TTA AAC GTT TTC AAC CAA TCA GTA GTA GAC TCA CAA
Ser Thr Met Ala Phe Asn Leu Asn Val Phe Asn Gln Ser Val Val Asp Ser Gln  310

.950
GGT CGT GTA CTA AAC ACT TGG GCA GAC ATC ATC AAC CGT GCT AAC TTA GGT ATG GAA GTA
Gly Arg Val Leu Asn Thr Trp Ala Asp Ile Ile Asn Arg Ala Asn Leu Gly Met Glu Val  330
                                    Ile

.1000
ATG CAC GAG CGT AAC GCT CAC AAC TTC CCT CTA GAC TTA GCT TCA ACT AAC TCT AGC TCA
Met His Glu Arg Asn Ala His Asn Phe Pro Leu Asp Leu Ala Ser Thr Asn Ser Ser Ser  350
                                                        Ala Ile Glu Ala Pro
                                                                         .1100
AAC AAC TAA TTT TTTTTTAAACTAAAATCTGTGTTAACCATACCTAGTTTATTTTAGTTTATACACACTTTT
Asn Asn *Oc                                                      ─────────────
Thr     Gly *Oc                                                       S1
                                 ←─────────────────────
                                 ─────────────────────→
              .1150
CATATATATATACTTAATAGCTACCATAGGCAGTTGGCAGGACGTCCC
```

FIG. 3C

TS = transcription start and transcription stop

```
  1 ATG GGC CAT CAT CAT CAT CAT CAT AGC AGC GGT CAT ATC GAA GGT CGT   60
  1  M   G   H   H   H   H   H   H   S   S   G   H   I   E   G   R    20

61 CAT ATG GCG ACT GAG TCC TCG GCC CCG GCG GCC ACC CAG AGC GCC ACC CCG  120
 21  H   M   A   T   E   S   S   A   P   A   A   T   Q   S   A   T   P   40

121 CTG GCG AAC TCG CTG TAC GTC GGT GAC CTG GAG AAG GAT GTC ACC GAG GCC CAG CTG  180
 41  L   A   N   S   L   Y   V   G   D   L   E   K   D   V   T   E   A   Q   L  60

181 TTC GAG CTC TTC TCC TCG GTT GGC CCT GTG GCC TCC ATT CGC GTG TGC CGC GAT GCC GTC  240
 61  F   E   L   F   S   S   V   G   P   V   A   S   I   R   V   C   R   D   A   V   80

241 ACG CGC CGC TCG CTG GGC TAC GCC TAC GTC AAC TAC AAC AGC GCT CTG GAC CCC CAG GCT  300
 81  T   R   R   S   L   G   Y   A   Y   V   N   Y   N   S   A   L   D   P   Q   A  100

301 GCT GAC CGC GCC ATG GAG ACC CTG AAC TAC CAT GTC GTC AAG GGC GTC AAG CCT ATG CGC ATC  360
101  A   D   R   A   M   E   T   L   N   Y   H   V   V   K   G   V   K   P   M   R   I  120

361 ATG TGG TCG CAC CGC GAC CCT TCG CGC GCC CGC AAG TCG GGC GTC GGC AAC ATC TTC ATC AAG  420
121  M   W   S   H   R   D   P   S   R   A   R   K   S   G   V   G   N   I   F   I   K  140

421 AAC CTG GAC AAG ACC ATC GAC AAG GCC CTG CAC CTG GTG TCG CAG ACC TTC GCC TAC GGC AAG  480
141  N   L   D   K   T   I   D   K   A   L   H   D   T   V   S   Q   T   F   A   Y   G  160

481 ATT CTG TCC TGC AAG GTT GCC ACT GAC GCC AAC GGC GTG TCG AAG GGC TAC GGC TTC GTG  540
161  I   L   S   C   K   V   A   T   D   A   N   G   V   S   K   G   Y   G   F   V  180

541 CAC TTC GAG GAC CAG GCC GCC GCT GAT CGC GCC ATT CAG ACC GTC AAC CAG AAG AAG ATT  600
181  H   F   E   D   Q   A   A   A   D   R   A   I   Q   T   V   N   Q   K   K   I  200

601 GAG GGC AAG ATC GTG TAC GTG GCC CCC TTC CAG AAG CGC CGC GCT GAC CGC CCC AGG GCA AGG  660
201  E   G   K   I   V   Y   V   A   P   F   Q   K   R   R   A   D   R   P   R   A   R  220
```

FIG. 5A

```
661  ACG TTG TAC ACC AAC GTG TTC GTC AAG AAC TTG CCG GCC GAC ATC GGC GAC GAG CTG   720
221   T   L   Y   T   N   V   F   V   K   N   L   P   A   D   I   G   D   E   L   240

721  GGC AAG ATG GCC ACC GAG CAC GGC GAG ATC ACC AGC GTC ATG GTG AAG GAC AAG       780
241   G   K   M   A   T   E   H   G   E   I   T   S   V   M   V   K   D   K       260

781  GGC AGC AAG TTC GGC TTC ATC AAC TTC AAG GAC GCC GAG TCG GCC AAG TGC           840
261   G   S   K   F   G   F   I   N   F   K   D   A   E   S   A   K   C           280

841  GTG GAG TAC CTG AAC GAG CGC GAG ATG CTG CGC CAG AGC GAG AGC AGC GCC CAG       900
281   V   E   Y   L   N   E   R   E   M   L   R   Q   S   E   S   K   A   Q       300

901  AAG AAG ACC GAG CGC CAG GCG ATG AAC CTG TAC GTC AAG AAC CGC CGC               960
301   K   K   T   E   R   Q   A   M   N   L   Y   V   K   N   Q   K   E   R       320

961  TAC CTG AAG TAC CAG CGT GAG TCT GGC TTC GTG ACC ATC TGC GAC CTG GAC          1020
321   Y   L   K   Y   Q   R   E   S   G   F   V   T   I   C   D   L   E   D       340

1021 GAC GAC GCC GCG CTG CGT AAG GGC TTC TCC ACC TTC ACC AGC TGC AAG GTC ATG     1080
341   D   D   A   A   L   R   K   G   F   S   T   F   T   S   C   K   V   M     360

1081 AAG GAC GGC AGC AAG GGC TTC GCC TTC GTG AAC ATG ATG ACC AGC AAG GCC CCC CTG TAC  1140
361   K   D   G   S   K   G   F   A   F   V   N   M   M   V   K   G   K   P   L   Y   380

1141 GCC ACC CGG CCG GTG ACC CGG ACC ATC TCG ACC TCG AAG GTC CAG CAC GAG        1200
381   A   T   R   P   V   T   R   T   I   S   T   S   K   V   Q   H   D   E      400

1201 GTG GCC CTG GCG CAG CGC AAG GAC GTG CGC CGT GCC ACC CAG CTG TAC ATG         1260
401   V   A   L   A   Q   R   K   D   V   R   R   A   T   Q   L   Y   M   Q      420

1261 GCG CGC ATG TAA GGATCC                                                      1278
421   A   R   M   *                                                              424
```

FIG. 5B

TS = transcription start and transcription stop

Bacterial luciferase A and B proteins expressed from a single mRNA containing the psbA 5' UTR with translational activator element.

RNA BINDING PROTEIN AND BINDING SITE USEFUL FOR EXPRESSION OF RECOMBINANT MOLECULES

This application is a divisional of application Ser. No. 09/341,550, filed Jul. 13, 1999, now U.S. Pat. No. 6,156,517, issued on Dec. 5, 2000, which is a national stage application of international application PCT/US98/00840, filed Jan. 16, 1998 and published in English, which claims priority, under 35 U.S.C. §119(e), to provisional application No. 60/035,955, filed Jan. 17, 1997, now abandoned, and provisional application No. 60/069,400, filed Dec. 12, 1997, now abandoned.

TECHNICAL FIELD

The invention relates to expression systems and methods for expression of desired genes and gene products in cells. Particularly, the invention relates to a gene encoding a RNA binding protein useful for regulating gene expression in cells, the protein binding site, a gene encoding a regulating protein disulfide isomerase and methods and systems for gene expression of recombinant molecules.

BACKGROUND

Expression systems for expression of exogenous foreign genes in eukaryotic and prokaryotic cells are basic components of recombinant DNA technology. Despite the abundance of expression systems and their wide-spread use, they all have characteristic disadvantages. For example, while expression in *E. coli* is probably the most popular as it is easy to grow and is well understood, eukaryotic proteins expressed therein are not properly modified. Moreover, those proteins tend to precipitate into insoluble aggregates and are difficult to obtain in large amounts. Mammalian expression systems, while practical on small-scale protein production, are more difficult, time-consuming and expensive than in *E. coli*.

A number of plant expression systems exist as well as summarized in U.S. Pat. No. 5,234,834, the disclosures of which are hereby incorporated by reference. One advantage of plants or algae in an expression system is that they can be used to produce pharmacologically important proteins and enzymes on a large scale and in relatively pure form. In addition, micro-algae have several unique characteristics that make them ideal organisms for the production of proteins on a large scale. First, unlike most systems presently used to produce transgenic proteins, algae can be grown in minimal media (inorganic salts) using sunlight as the energy source. These algae can be grown in contained fermentation vessels or on large scale in monitored ponds. Ponds of up to several acres are routinely used for the production of micro-algae. Second, plants and algae have two distinct compartments, the cytoplasm and the chloroplast, in which proteins can be expressed. The cytoplasm of algae is similar to that of other eukaryotic organisms used for protein expression, like yeast and insect cell cultures. The chloroplast is unique to plants and algae and proteins expressed in this environment are likely to have properties different from those of cytoplasmically expressed proteins.

The present invention describes an expression system in which exogenous molecules are readily expressed in either prokaryotic or eukaryotic hosts and in either the cytoplasm or chloroplast. These beneficial attributes are based on the discovery and cloning of components of translation regulation in plants as described in the present invention.

Protein translation plays a key role in the regulation of gene expression across the spectrum of organisms (Kozak, *Ann. Rev. Cell Biol.*, 8:197–225 (1992) and de Smit and Van Duin, *Prog. Nucleic Acid Res. Mol. Biol.*, 38:1–35 (1990)). The majority of regulatory schemes characterized to date involve translational repression often involving proteins binding to mRNA to limit ribosome association (Winter et al., *Proc. Natl. Acad. Sci., USA*, 84:7822–7826 (1987) and Tang and Draper, *Biochem.*, 29:4434–4439 (1990)). Translational activation has also been observed (Wulczyn and Kahmann, *Cell*, 65:259–269 (1991)), but few of the underlying molecular mechanisms for this type of regulation have been identified. In plants, light activates the expression of many genes. Light has been shown to activate expression of specific chloroplast encoded mRNAs by increasing translation initiation (Mayfield et al., *Ann. Rev. Plant Physiol. Plant Mol. Biol.*, 46:147–166 (1995) and Yohn et al., *Mol. Cell Biol.*, 16:3560–3566 (1996)). Genetic evidence in higher plants and algae has shown that nuclear encoded factors are required for translational activation of specific chloroplast encoded mRNAs (Rochaix et al., *Embo J.*, 8:1013–1021 (1989), Kuchka et al., *Cell*, 58:869–876 (1989), Girard-Bascou et al., *Embo J.*, 13:3170–3181 (1994), Kim et al., *Plant Mol. Biol.*, 127:1537–1545 (1994).

In the green algae *Chlamydomonas reinhardtii*, a number of nuclear mutants have been identified that affect translation of single specific mRNAs in the chloroplast, often acting at translation initiation (Yohn et al., supra, (1996)). Mutational analysis of chloroplast mRNAs has identified sequence elements within: the 5' untranslated region (UTR) of mRNAs that are required for translational activation (Mayfield et al., supra, (1995), Mayfield et al., *J. Cell Biol.*, 127:1537–1545 (1994) and Rochaix, *Ann. Rev. Cell Biol.*, 8:1–28 (1992)), and the 5' UTR of a chloroplast mRNA can confer a specific translation phenotype on a reporter gene in vivo (Zerges and Rochaix, *Mol. Cell Biol.*, 14:5268–5277 (1994) and Staub and Maliga, *Embo J.*, 12:601–606 (1993).

Putative translational activator proteins were identified by purifying a complex of four proteins that binds with high affinity and specificity to the 5' UTR of the chloroplast encoded psbA mRNA [encoding the D1 protein, a major component of Photosystem II (PS II)] (Danon and Mayfield, *Embo J.*, 10:3993–4001 (1991)). Binding of these proteins to the 5' UTR of psbA mRNA correlates with translation of this mRNA under a variety of physiological (Danon and Mayfield, id., (1991)) and biochemical conditions (Danon and Mayfield, *Science*, 266:1717–1719 (1994) and Danon and Mayfield, *Embo J.*, 13:2227–2235 (1994)), and in different genetic backgrounds (Yohn et al., supra, (1996)). The binding of this complex to the psbA mRNA can be regulated in vitro in response to both redox potential (Danon and Mayfield, *Science*, 266:1717–1719 (1994)) and phosphorylation (Danon and Mayfield, *Embo J.*, 1–3:2227–2235 (1994)), both of which are thought to transduce the light signal to activate translation of psbA mRNA. The 47 kDa member of the psbA RNA binding complex (RB47) is in close contact with the RNA, and antisera specific to this protein inhibits binding to the psbA mRNA in vitro (Danon and Mayfield, supra, (1991)).

Although the translational control of psbA mRNA by RB47 has been reported, the protein has not been extensively characterized and the gene encoding RB47 has not been identified, cloned and sequenced. In addition, the regulatory control of the activation of RNA binding activity to the binding site by nuclear-encoded trans-acting factors, such as RB60, have not been fully understood. The present invention now describes the cloning and sequencing of both RB47 and RB60. Based on the translation regulation mechanisms of RB47 and RB60 with the RB47 binding site, the present invention also describes a translation regulated expression system for use in both prokaryotes and eukaryotes.

BRIEF DESCRIPTION OF THE INVENTION

The RB47 gene encoding the RB47 activator protein has now been cloned and sequenced, and the target binding site for RB47 on messenger RNA (mRNA) has now been identified. In addition, a regulatory protein disulfide isomerase, a 60 kilodalton protein referred to as RB60, has also been cloned, sequenced and characterized. Thus, the present invention is directed to gene expression systems in eukaryotic and prokaryotic cells based on translational regulation by RB47 protein, its binding site and the RB60 regulation of RB47 binding site activation.

More particularly, the present invention describes the use of the RB47 binding site, i.e., a 5' untranslated region (UTR) of the chloroplast psbA gene, in the context of an expression system. for regulating the expression of genes encoding a desired recombinant molecule. Protein translation is effected by the combination of the RB47 binding site and the RB47 binding protein in the presence of protein translation components. Regulation can be further imposed with the use of the RB60 regulatory protein disulfide isomerase. Therefore, the present invention describes reagents and expression cassettes for controlling gene expression by affecting translation of a coding nucleic acid sequence in a cell expression system.

Thus, in one embodiment, the invention contemplates a RB47 binding site sequence, i.e., a mRNA sequence, typically a mRNA leader sequence, which contains the RB47 binding site. A preferred RB47 binding site is psbA mRNA. For use in expressing recombinant molecules, the RB47 binding site is typically inserted 5' to the coding region of the preselected molecule to be expressed. In a preferred embodiment, the RB47 binding site is inserted into the 5' untranslated region along with an upstream psbA promoter to drive the expression of a preselected nucleic acid encoding a desired molecule. In alternative embodiments, the RB47 binding site is inserted into the regulatory region downstream of any suitable promoter present in a eukaryotic or prokaryotic expression vector. Preferably, the RB47 binding site is positioned within 100 nucleotides of the translation initiation site. In a further aspect, 3' to the coding region is a 3' untranslated region (3' UTR) necessary for transcription termination and RNA processing.

Thus, in a preferred embodiment, the invention contemplates an expression cassette or vector that contains a transcription unit constructed for expression of a preselected nucleic acid or gene such that upon transcription, the resulting mRNA contains the RB47 binding site for regulation of the translation of the preselected gene transcript through the binding of the activating RB47 protein. The RB47 protein is provided endogenously in a recipient cell and/or is a recombinant protein expressed in that cell.

Thus, the invention also contemplates a nucleic acid molecule containing the sequence of the RB47 gene. The nucleic acid molecule is preferably in an expression vector capable of expressing the gene in a cell for use in interacting with a RB47 binding site. The invention therefore contemplates an expressed recombinant RB47 protein. In one embodiment, the RB47 binding site and RB47 encoding nucleotide sequences are provided on the same genetic element. In alternative embodiments, the RB47 binding site and RB47 encoding nucleotide sequences are provided separately.

The invention further contemplates a nucleic acid molecule containing the sequence encoding the 69 kilodalton precursor to RB47. In alternative embodiments, the RB47 nucleic acid sequence contains a sequence of nucleotides to encode a histidine tag. Thus, the invention relates to the use of recombinant RB47, precursor RB47, and histidine-modified RB47 for use in enhancing translation of a desired nucleic acid.

The invention further contemplates a nucleic acid molecule containing a nucleotide sequence of a polypeptide which regulates the binding of RB47 to RB47 binding site. A preferred regulatory molecule is the protein disulfide isomerase RB60. The RB60-encoding nucleic acid molecule is preferably in an expression vector capable of expressing the gene in a cell for use in regulating the interaction of RB47 with a RB47 binding site. Thus, the invention also contemplates an expressed recombinant RB60 protein. In one embodiment, the RB47 binding site, RB47 encoding and RB60 encoding nucleotide sequences are provided on the same genetic element. In alternative embodiments, the expression control nucleotide sequences are provided separately. In a further aspect, the RB60 gene and RB47 binding site sequence are provided on the same construct.

The invention can therefore be a cell culture system, an in vitro expression system or a whole tissue, preferably a plant, in which the transcription unit is present that contains the RB47 binding site and further includes a (1) transcription unit capable of expressing RB47 protein or (2) the endogenous RB47 protein itself for the purpose of enhancing translation of the preselected gene having an RB47 binding site in the mRNA. Preferred cell culture systems are eukaryotic and prokaryotic cells. Particularly preferred cell culture systems include plants and more preferably algae.

A further preferred embodiment includes (1) a separate transcription unit capable of expressing a regulatory molecule, preferably RB60 protein, or (2) the endogenous RB60 protein itself for the purpose of regulating translation of the preselected gene having an RB47 binding site in the mRNA. In an alternative preferred embodiment, one transcription unit is capable of expressing both the RB47 and RB60 proteins. In a further aspect, the RB47 binding site sequence and RB60 sequence are provided on the same construct.

In one aspect of the present invention, plant cells endogenously containing RB47 and RB60 proteins are used for the expression of recombinant molecules, such as proteins or polypeptides, through activation of the RB47 binding in an exogenously supplied expression cassette. Alternatively, stable plant cell lines containing endogenous RB47 and RB60 are first generated in which RB47 and/or RB60 proteins are overexpressed. Overexpression is obtained preferably through the stable transformation of the plant cell with one or more expression cassettes for encoding recombinant RB47 and RB60. In a further embodiment, stable cell lines, such as mammalian or bacterial cell lines, lacking endogenous RB47 and/or RB60 proteins are created that express exogenous RB47 and/or RB60.

Plants for use with the present invention can be a transgenic plant, or a plant in which the genetic elements of the invention have been introduced. Based on the property of controlled translation provided by the combined use of the RB47 protein and the RB47 binding site, translation can be regulated for any gene product, and the system can be introduced into any plant species. Similarly, the invention is useful for any prokaryotic or eukaryotic cell system.

Methods for the preparation of expression vectors is well known in the recombinant DNA arts, and for expression in plants is well known in the transgenic plant arts. These particulars are not essential to the practice of the invention, and therefore will not be considered as limiting.

The invention allows for high level of protein synthesis in plant chloroplasts and in the cytoplasm of both prokaryotic and eukaryotic cells. Because the chloroplast is such a productive plant organ, synthesis in chloroplasts is a preferred site of translation by virtue of the large amounts of protein that can be produced. This aspect provides for great advantages in agricultural production of mass quantities of a preselected protein product.

The invention further provides for the ability to screen for agonists or antagonists of the binding of RB47 to the RB47 binding site using the expression systems as described herein. Antagonists of the binding are useful in the prevention of plant propagation.

Also contemplated by the present invention is a screening assay for agonists or antagonists of RB60 in a manner analogous to that described above for RB47. Such agonists or antagonists would be useful in general to modify expression of RB60 as a way to regulate cellular processes in a redox manner.

Kits containing expression cassettes and expression systems, along with packaging materials comprising a label with instructions for use, as described in the claimed embodiments are also contemplated for use in practicing the methods of this invention.

Other uses will be apparent to one skilled in the art in light of the present disclosures.

BRIEF DESCRIPTION OF THE DRAWINGS

In the figures forming a portion of this disclosure:

FIGURES 1A–1D show the complete protein amino acid residue sequence of RB47 is shown from residues 1–623, together with the corresponding nucleic acid sequence encoding the RB47 sequence, from base 1 to base 2732. The nucleotide coding region is shown from base 197–2065, the precursor form. The mature form is from nucleotide position 197–1402. Also shown is the mRNA leader, bases 1–196, and poly A tail of the mRNA, bases 2066–2732. Both the nucleotide and amino acid sequence are listed in SEQ ID NO 5.

FIGS. 2A–2B show the complete protein amino acid residue sequence of RB60 is shown from residues 1–488, together with the corresponding nucleic acid sequence from base 1 to base 2413, of which bases 16–1614 encode the RB60 sequence. Both the nucleotide and amino acid sequence are listed in SEQ ID NO 10.

FIGS. 3A–3C show the complete sequence of the psbA mRNA, showing both encoded psbA protein amino acid residue sequence (residues 1–352) and the nucleic acid sequence as further described in Example 3 is illustrated. Both the nucleotide and amino acid sequence are listed in SEQ ID NO 13.

FIGS. 5A–5B show the nucleotide and amino acid sequence of the RB47 molecule containing a histidine tag, the sequences of which are also listed in SEQ ID NO 14.

DETAILED DESCRIPTION OF THE INVENTION

A. Definitions

TABLE OF CORRESPONDENCE

Figure 3A:
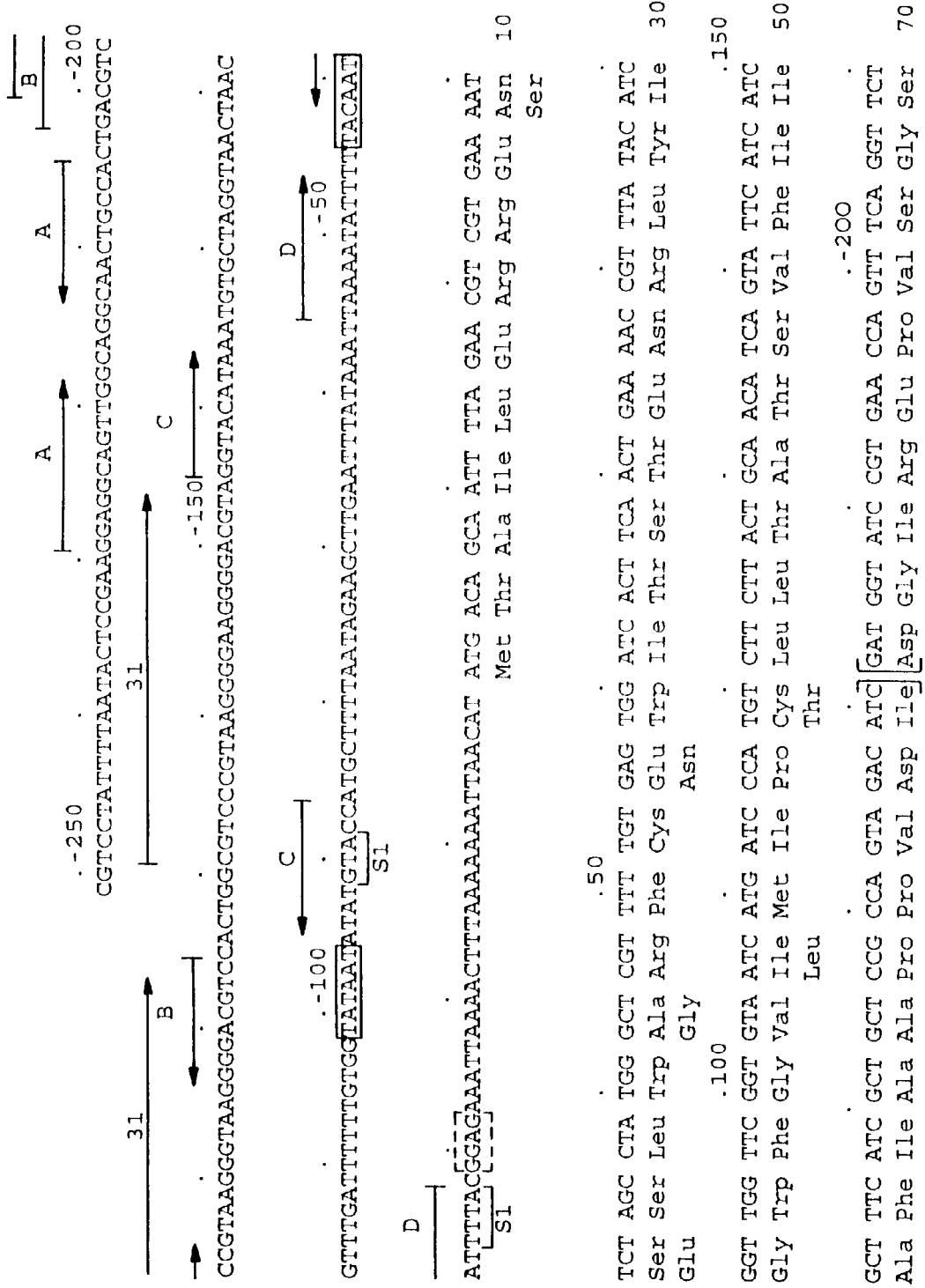

| Code Group | | Nucleotide(s) |
|---|---|---|
| A | A | adenine |
| C | C | cytosine |
| G | G | guanine |

-continued

TABLE OF CORRESPONDENCE

| Code | Group | Nucleotide(s) |
|---|---|---|
| T | T | thymine (in DNA) |
| U | U | uracil (in RNA) |
| Y | C or T(U) | pyrimidine |
| R | A or G | purine |
| M | A or C | amino |
| K | G or T(U) | keto |
| S | G or C | strong interaction (3 hydrogen bonds) |
| W | A or T(U) | weak interaction (2 hydrogen bonds) |
| H | A or C or T(U) | not-G |
| B | G or T(U) or C | not-A |
| V | G or C or A | not-T or not-U |
| D | G or A or T(U) | not-C |
| N | G, A, C or T(U) | any |

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as lona as the desired functional property is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 CFR §1.822(b)(2)), abbreviations for amino acid residues are shown in the following Table of Correspondence:

TABLE OF CORRESPONDENCE

SYMBOL

| 1-Letter | 3-Letter | AMINO ACID |
|---|---|---|
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | unknown/other |

In addition the following have the meanings below:

| BOC | tert-butyloxycarbonyl |
|---|---|
| DCCI | dicylcohexylcarbodiimide |

-continued

| DMF | dimethylformamide |
|---|---|
| OMe | methoxy |
| HOBt | 1-hydroxybezotriazole |

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino acid residues.

Polypeptide: A linear series of amino acid residues connected to one another by peptide bonds between the alpha-amino group and carboxy group of contiguous amino acid residues.

Peptide: A linear series of no more than about 50 amino acid residues connected one to the other as in a polypeptide.

Protein: A linear series of greater than 50 amino acid residues connected one to the other as in a polypeptide.

Synthetic peptide: A chemically produced chain of amino acid residues linked together by peptide bonds that is free of naturally occurring proteins and fragments thereof.

Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and their grammatical equivalents, and is represented herein by a sequence whose left to right orientation is in the conventional direction of 5'-terminus to 3'-terminus.

Base Pair (bp): A partnership of adenine (A) with thymine (T), or of cytosine (C) with guanine (G) in a double stranded DNA molecule. In RNA, uracil (U) is substituted for thymine.

Nucleic Acid: A polymer of nucleotides, either single or double stranded.

Polynucleotide: A polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, probes, RNA/DNA segments, oligonucleotides or "oligos" (relatively short polynucleotides), genes, vectors, plasmids, and the like.

Gene: A nucleic acid whose nucleotide sequence codes for an RNA or polypeptide. A gene can be either RNA or DNA.

Duplex DNA: A double-stranded nucleic acid molecule comprising two strands of substantially complementary polynucleotides held together by one or more hydrogen bonds between each of the complementary bases present in a base pair of the duplex. Because the nucleotides that form a base pair can be either a ribonucleotide base or a deoxyribonucleotide base, the phrase "duplex DNA" refers to either a DNA-DNA duplex comprising two DNA strands (ds DNA), or an RNA-DNA duplex comprising one DNA and one RNA strand.

Complementary Bases: Nucleotides that normally pair up when DNA or RNA adopts a double stranded configuration.

Complementary Nucleotide Sequence: A sequence of nucleotides in a single-stranded molecule of DNA or RNA that is sufficiently complementary to that on another single strand to specifically hybridize to it with consequent hydrogen bonding.

Recombinant DNA (rDNA) molecule: A DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evoluzionarily different, are said to be "heterologous".

Vector: A rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors".

Conserved: A nucleotide sequence is conserved with respect to a preselected (reference) sequence if it non-randomly hybridizes to an exact complement of the preselected sequence.

Hybridization: The pairing of substantially complementary nucleotide sequences (strands of nucleic acid) to form a duplex or heteroduplex by the establishment of hydrogen bonds between complementary base pairs. It is a specific, i.e., non-random, interaction between two complementary polynucleotides that can be competitively inhibited.

Nucleotide Analog: A purine or pyrimidine nucleotide that differs structurally from A, T, G, C, or U, but is sufficiently similar to substitute for the normal nucleotide in a nucleic acid molecule.

Upstream: In the direction opposite to the direction of DNA transcription, and therefore going from 5' to 3' on the noncoding strand, or 3' to 5' on the RNA transcript.

Downstream: Further along a DNA sequence in the direction of sequence transcription or read out, that is, traveling in a 3'- to 5'-direction along the noncoding strand of the DNA or 5'- to 3'-direction along the RNA transcript.

Stop Codon: Any of three codons that do now code for an amino acid, but instead cause termination of protein synthesis. They are UAG, UAA and UGA and are also referred to as a nonsense, termination, or translational stop codon.

Reading Frame: Particular sequence of contiguous nucleotide triplets (codons) employed in translation. The reading frame depends on the location of the translation initiation codon.

Homolog: Refers to a molecules that is structurally or functionally equivalent to a molecule of the present invention.

Fusion Protein: A polypeptide produced by recombinant DNA methods in which a first polypeptide domain is operatively linked to a second polypeptide domain by the peptide bond produced through expression of a single open reading frame to express a single "fused" polypeptide.

Chimeric Molecule: A bifunctional molecule formed by connecting two separate molecules through chemical linkage, such as by crosslinking two isolated polypeptides or joining two heterologous fragments of DNA from different sources.

B. Translational Regulation by RB47 and RB60
1. RB47 and RB47 Binding Site

The present invention is based primarily on the discovery of that RB47, a mRNA binding protein, is a translational activator of the chloroplast psbA mRNA from *Chlamydomonas reinhardtii*, a green algae. The role of RB47 is now clearer, as evidence for its function comes from several independent sources. First, biochemical analysis has shown that this protein (along with other proteins within the complex) binds with high affinity and specificity to the psbA 5' UTR in a manner consistent with a role in translational regulation; high levels of binding are observed during high translation levels in the light, and low levels of binding are observed when translation is low in the dark. Second, the predicted amino acid sequence of RB47, now available since the cloning of RB47 as described herein, indicates the role this protein plays in translation. RB47 belongs to a family of proteins known as poly(A) binding proteins that bind RNA and have been shown to play a role in translation initiation (Bag and Wu, *Eur. J. Biochem.*, 237:143–152 (1996); de Melo Neto et al., *Nuc. Acids Res.*, 23:2198–2205 (1995); Proweller and Butler, *J. Biol. Chem.*, 271:10859–10865 (1996); Sachs and Davis, *Cell*, 58:857–867 (1989); Tarun and Sachs, *Embo J.*, 15:7168–7177 (1996)). Finally, genetic analysis has predicted translational activators of chloroplast mRNAs (Girard-Bascou et al., *Curr. Genet.*, 22:47–52 (1992); Kuchka et al., *Embo J.*, 7:319–324 (1988); Rochaix et al., *Ann. Rev. Cell Biol.*, 8:1–28 (1989); and Yohn et al., *Mol. Cell. Biol.*, 16:3560–3566 (1996)). With the use and characterization of the hf149 mutant, a high fluorescence phenotype of *C. reinhardtii*, the absence of RB47 has been shown to correspond directly to the loss of translational initiation of the psbA mRNA, thus defining RB47 as a translational activator of the psbA mRNA. This is further supported by an additional nuclear mutation in *C. reinhardtii* (hf261) which is non-allelic to hf149, but shows the similar phenotype of a specific loss of D1 translation. The RB47 protein accumulates to less than 10% of the wild type level in this mutant.

While proteins which bind to the 5' UTR of chloroplast mRNAs seem likely candidates for translational activators, no direct link had been made to the body of genetic data prior to the characterization of the hf149 mutant as described in the present invention. Thus, the identification of RB47, the cloning thereof, and the role of RB47 in translation activation of psbA are novel and form the basis of the mechanisms of the expression cassettes of the present invention.

hf149 is not likely to be a mutation directly in the RB47 gene, as Southern and Northern analysis indicates that the RB47 gene is intact and produces normal amounts of RB47 mRNA in the hf149 strain. This leaves open the possibility that the loss of RB47 protein is the result of a loss of psbA translation, rather than the cause of it. Although this is a formal possibility, it is highly unlikely given the fact that the RB47 protein accumulates in other psbA translation initiation deficient mutants (e.g. F35, Yohn et al., *Mol. Cell Biol.*, 16:3560–1566 (1996)), and that the psbA RB60 RNA binding protein still accumulates in the hf149 strain. thus, the hf149 mutation provides strong evidence that the RB47 protein is directly involved in translational regulation of the chloroplast encoded psbA mRNA. Identification of the specific defect in the hf149 mutant should yield further insights into this process.

The dramatic reduction in the amount of psbA mRNA associated with ribosomes in the hf149 mutation suggests that RB47 is specifically required for ribosomes to initiate translation with the psbA mRNA. Although the identification of a message specific translational activator in the chloroplast has not previously been shown, other organellar systems may use similar mechanisms for controlling and coordinating gene expression, most notably the mitochondria of yeast. In particular, the COX3 mRNA of *Saccharomyces cerevisiae* is translationally regulated by a complex of at least three proteins which have been shown genetically (Wiesenberger et al., *Mol. Cell Biol.*, 15:3291–3300 (1995)) and biochemically (Brown et al., *Mol. Cell Biol.*, 14:1045–1053 (1994)) to interact with each other and with the COX3 mRNA. One of these proteins (PET122) also interacts with the mitochondrial ribosome (Haffter et al., *Genetics*, 127:319–326 (1991); Haffter et al., *Genetics*, 125:495–503 (1990); McMullin et al., *Mol. Cell Biol.*, 10:4590–4595 (1990)), suggesting a model for translational activation in which these proteins facilitate the initial interaction between the mRNA and the ribosome. A similar mechanism may be involved with RB47, the psbA mRNA and chloroplast ribosomes.

The identification of RB47 as a poly(A) binding protein (PABP) is somewhat unexpected given that translation in the chloroplast is generally considered prokaryotic like, and PABPs have not been identified as components of the prokaryotic translation apparatus. The chloroplast has 70S ribosomes (as in prokaryotes) and the mRNAs encoded by the chloroplast genome do not, in general, have poly(A) tails, and often contain prokaryotic consensus ribosome binding sequences (Gillham et al., *Ann. Rev. Genetics*, 28:71–93 (1994); Harris et al., *Microbiol. Rev.*, 58:700–754 (1994)). The addition of A-rich sequences to the 3' end of endonucleolytic cleavage products of some chloroplast mRNAs has recently been described (Kudia et al., *Embo J.*, 15:7137–7146 (1996); Lisitsky et al., *Proc. Natl. Acad. Sci., USA*, 93:13398–13403 (1996)), and this seems to play a role in degradation of the RNA, as in prokaryotes. The identification of a PABP in the chloroplast indicates that components of the cytoplasmic translation machinery may have been appropriated by the chloroplast for a similar function. These data also indicate that PABPs may function in translational regulation in the chloroplast in a manner not previously described for cytoplasmic mRNAs, although the role of RB47 in psbA translation seems to fit with the limited information known about the function of PABPs in other systems. While no specific biochemical function has yet been identified for any member of the PABP family, these proteins have been defined as specific RNA binding proteins with a role in translational regulation. In yeast, PABP is essential for viability (Sachs et al., *Cell*, 45:827–835 (1986); Sachs et al., *Mol. Cell Biol.*, 7:3268–3276 (1987)), and a temperature sensitive (ts) allele of PABP shows that depletion of PABP in yeast results in inhibition of translation initiation and poly(A) tail shortening (Sachs and Davis, *Cell*, 58:857–867 (1989)). Further, revertants of this ts mutation mapped to a ribosomal protein, suggesting that PASP interacts with the ribosome to mediate translation initiation (Sachs and Davis, id., (1989)). In addition, PABPs have been shown to physically interact with ribosomes (Proweller and Butler, supra, (1996)), and with eukaryotic initiation factors (eIF4G) (Tarun and Sachs, supra, (1996)). RB47 appears to fit these general roles predicted for PABPs, with the exception that RB47 shows specific binding to the 5' UTR of the psbA mRNA, and that RB47 is acting in the chloroplast, where translation is distinct from that in the cytoplasm both spatially and mechanistically. However, the fact that this nuclear encoded, eukaryotic protein has been exploited for use in the chloroplast may not be too surprising given the bi-directional exchange of genetic information between the chloroplast and nucleus (Morden et al., *Biosystems*, 28:75–90 (1992)).

Thus, in view of the binding specificity of RB47 to the RB47 binding site in psbA mRNA, the present invention is unique in describing expression cassettes regulated at the translational level.

From the genetic, biochemical and molecular analysis of translational regulation in the chloroplast, a model for how the psbA mRNA binding proteins act in translation initiation and activation of psbA mRNA is presently formulated. In this model, nuclear encoded proteins, including the PABP homologue RB47, are transported into the chloroplast. Once in the plastid these proteins are activated to bind to RNA elements found within the 5' UTR of specific mRNAs (Mayfield et al., *J. Cell Biol.*, 127:1537–1545 (1994)). This activation of binding is light responsive via the reducing potential generated by the light reactions of photosynthesis (Danon and Mayfield, *Embo J.*, 13:2227–2235 (1994)). The interaction of the translational activator proteins and cis-acting RNA elements facilitates the initial interaction of the message with ribosomal subunits, resulting in increased translation of the D1 protein from the psbA mRNA.

Thus, in view of the enhancement of translation by the binding of a translation activator protein on a RNA element and in view of the cloning of both RB47 and RB60 translation activator proteins, the present invention contemplates the following aspects related to expression systems and uses thereof: isolated nucleic acids encoding recombinant proteins and variations thereof; the recombinant proteins themselves; use of the RNA binding site element in concert with the RB47 and RB60 nucleic acids and proteins thereof including endogenously expressed counterparts; expression cassettes in which the genetic elements of this invention are operably linked; expression systems including cells in vitro and in vivo; methods of use thereof for expressing a heterologous molecule and for screening for agonists and antagonists of the interaction on which the present invention is based; and lastly, kits for use in expression of proteins and preparation of RNA transcripts.

The present invention therefore describes the use of an RB47 binding site nucleotide sequence and a coordinate RB47 binding site molecule for the purpose of enhancing translation of a desired heterologous coding sequence, thereby producing the desired expressed molecule for use thereafter.

Based on the translational activation mediated through the binding of an RB47 binding site sequence, typically a mRNA sequence, the present elements of RB47 binding site and an RB47 binding site polypeptide are therefore referred to as a translational activation system. The system is capable of further modulation or regulation by a polypeptide that regulates the binding of a RB47 binding site interaction with its activator protein as discussed in the next section. In a preferred embodiments, the translational activator protein of RB47 binding site is RB47 and the translation regulatory molecule that regulates the binding of an activator to an RB47 binding site is RB60, the latter of which is discussed below.

Thus, a molecule that binds RB47 and results in the translational activation of RB47 binding site thereby enhancing translation of a desired mRNA sequence is referred to as a RB47 binding site polypeptide. Preferably, the polypeptide is RB47 that is present endogenously, i.e., naturally occurring, in a cell such that activation of a RB47 binding site occurs through an interaction of an endogenous protein with an exogenously provided RB47 binding site sequence as further described below. Functional RB47 protein is found in plant chloroplasts as reviewed above.

In other embodiments, RB47 is a recombinant protein produced through the expression of the coding sequence in a recipient cell as discussed in Section C below. Expression of a recombinant RB47 is now possible in view of the cloning of the cDNA encoding of RB47 as described in the present invention and in Examples 2 and 3. Exemplary recombinant RB47 proteins produced by the methods of this invention, more completely described in the Examples, include mature or processed RB47 that is approximately a 47 kilodalton (kDa) protein, precursor or unprocessed RB47 that is approximately a 69 kDa protein, and a histidine-modified RB47 protein that is also approximately a 47 kDa protein, the latter of which is useful for purification aspects as described in the Examples.

Thus, although the preferred RB47 proteins and nucleic acid compositions are derived from *Chlamydomonas reinhardtii* as discussed in the present invention, variations at both the amino acid and nucleotide sequence level may exist in similar functioning molecules isolated from different algae species as well as within differing plant geni. Such variations are not to be construed as limiting. For example, allelic variation within a plant species can tolerate a several percent difference between isolates of a type of RB47, the differences of which comprise non-deleterious variant amino acid residues. Thus a protein of about 95% homology, and preferably at least 98% homology, to a disclosed RB47 protein is considered to be an allelic variant of the disclosed RB47 protein, and therefore is considered to be a RB47 protein of this invention.

Thus, the term "homolog" refers to any RB47-like protein or polypeptide having similar three-dimensional structure based on the amino acid residue sequence that can be encoded by differing specific nucleic acid sequences. In other words, the RB47 species of this invention are homologous molecules in view of the amino acid sequence similarity, the presence of a species specific sequence, the overall secondary and tertiary structure of the molecule, and the like physical parameters.

Thus as used herein, the phrases "RB47 protein" and "RB47 peptide or polypeptide" refers to a RB47 molecule having an amino acid residue sequence that comprises an amino acid residue sequence that corresponds, and preferably is identical, to a portion of a RB47 protein, either produced endogenously or exogenously to produce recombinant proteins, of this invention.

A recombinant RB47 protein need not necessarily be substantially pure, or even isolated, to be useful in certain embodiments, although recombinant production methods are a preferred means to produce a source for further purification to yield an isolated or substantially pure receptor composition. A recombinant RB47 protein can be present in or on a mammalian cell line or in crude extracts of a mammalian cell line. In other embodiments, a recombinant RB47 protein is produced in or on plants or plant cell lines, for subsequent use therein to activate the translation of a desired coding sequence as described in Section C. Preferred expression vector systems for production of RB47 proteins of this invention in this context are described in Section C and in the Examples.

In the context of the present translational activation system of this invention, the presence of a RB47 binding site sequence is required. Thus, a RB47 binding site sequence is referred to as a translational activation binding domain, the activation of which leads to the enhanced or increased translation of a desired coding sequence. As previously discussed, endogenous activation of the RB47 mRNA binding sequence in the psbA gene in green algae chloroplast by RB47 results in the expression of D1 protein. As further discussed below, this translation activation can be further modulated or regulated by RB60. The nucleotide sequence in the 5' untranslated (5' UTR) end of the psbA gene containing the RB47 binding site is described in Example 3. The use of the RB47 binding site sequence thus is contemplated for use in preparing an expression cassette of this invention as further described in Section C and more completely in the Examples. Insofar as the binding of a RB47 binding site polypeptide to the nucleotide sequence of the RB47 binding site allows for translational activation of an encoding mRNA, variations, substitutions, additions, deletions and the like permutations in the nucleic acid sequence of the RB47 nucleic acid sequence are contemplated for use in the present invention. In addition, any functional RB47 binding site nucleotide sequence is generally positioned upstream, i.e., 5', to the desired coding nucleotide sequence and in relation to the other inserted genetic elements including an upstream promoter, transcription initiation sites and downstream translation initiation sites of a coding region that can be a desired coding sequence or one of the genetic control elements of the invention, such as RB47 or RB60, as further described In Section C. and in the Examples.

2. RB60

Light-regulated translation of chloroplast mRNAs requires trans-acting factors that interact with the 5' untranslated region (UTR) of these mRNAs. The present invention describes a protein disulfide isomerase (PDI), also referred to as RB60, that is localized to the chloroplast and co-purifies with cPABP. The cDNA encoding the RB60 protein has now been cloned as described herein. As described more fully below, the RB60 protein has now been shown to modulate the binding of RB47, the cPABP, to the 5' UTR of the psbA mRNA by reversibly changing the redox status of cPABP using redox potential or ADP-dependent phosphorylation. This mechanism allows for a simple reversible switch regulating gene expression in the chloroplast. Moreover, in view of the modulatory properties of RB60 as discussed below, incorporation of RB60 into the compositions and methods of this invention are valuable for regulating the expression of a desired gene product with the expression cassettes and systems of the present invention as described further herein and in the Examples.

The present inventors have determined the role of RB60 in regulating the binding of RB47 to psbA mRNA containing the RB47 binding site. The work has recently been published, Kim and Mayfield, *Science*, 278:1954–1957 (1997), references for the RB60 section herein are provided in the published paper. As previously discussed, synthesis of certain chloroplast photosynthetic proteins is activated 50–100 fold in response to light exposure without an increase in the corresponding mRNA levels, indicating that translation of chloroplast mRNAs is light-regulated. Genetic evidence has shown that nuclear-encoded trans-acting factors interact with the 5' untranslated region (UTR) of chloroplast mRNAs to activate translation of these mRNAs in a light-dependent fashion. A set of proteins (38, 47, 55 and 60 kDa) was identified to bind as a complex to the 5' UTR of the psbA mRNA, encoding the photosynthetic reaction center protein D1 from the green algae *Chlamydomonas reinhardtii*. Binding of this protein complex to the 5' UTR of the psbA mRNA correlates with light-enhanced translation of this mRNA under a variety of environmental condition, and in mutations deficient in psbA mRNA translation. RNA binding activity of the protein complex for the 5' UTR of the psbA mRNA can be regulated in vitro by at least two different mechanisms: ADP-dependent phosphorylation and changes in redox potential.

The present invention and the Kim and Mayfield, id., (1997) paper describe the cloning of the cDNA encoding the 60 kDa psbA mRNA binding protein (RB60) as further described in the Examples. The predicted amino acid sequence of the cloned cDNA is also described therein.

To verify that RB60 is localized to the chloroplasts, an immunoblot analysis of isolated pea chloroplasts was performed using the C. reinhardtii R360 antiserum. To confirm that the isolated pea chloroplasts were free of cytoplasmic contamination, immunoblot analysis was performed with antiserum against the large subunit of ribulose bisphosphate carboxylase (RuBPCase, located in chloroplast) and antiserum against the cytoplasmic protein tubuli. RuBPCase antiserum recognized proteins from both whole leaf extracts (cytoplasm plus chloroplast) and from isolated chloroplasts. The tubulin antiserum recognized a protein in whole leaf extracts, but not in the chloroplast fraction), showing that the isolated chloroplasts were free of cytoplasmic proteins. The protein extracts from isolated pea chloroplasts were enriched using heparin-agarose chromatography: enrichment was required for immunoblot assays with the RB60 antiserum as RB60 is a minor component within the chloroplast. Immunoblot analysis was performed on proteins from purified pea chloroplasts, from C. reinhardtii cell extracts isolated by heparin-agarose chromatography, and on recombinant RB60. A specific signal immunochemically related to RB60 was clearly detected at approximately 63 kDa in the pea chloroplast sample. A signal of equal intensity was observed for C. reinhardtii proteins and for the recombinant RB60.

Chloroplast PDI (CPDI) contains the two-CGHC- catalytic sites that are involved in the formation, reduction and isomerization of disulfide bonds associated with protein folding. The identification of these redox catalytic sites prompted the investigation of the role of RB60 in the redox-regulated binding of RB47 to the 5' UTR of the psbA mRNA. Both RB60 and RB47, containing only the four RNA recognition motif domains, were expressed as further described in the Examples in E. coli as a fusion protein with a histidine tag, purified on a Ni-NTA agarose affinity column and used for subsequent RNA binding gel mobility-shift assays. The effect of a reducing agent on RNA binding activity of recombinant RB47 (r-RB47) was assessed by the addition of DTT (dithiothreitol) in the presence of recombinant RB60 (r-RB60). r-RB47 was preincubated with 10 mM DTT, a 5-fold excess of r-RB60 alone, or both DTT plus r-RB60, prior to adding a $^{32}$P-labeled 5'-UTR of the psbA mRNA, followed by a gel mobility-shift assay. The results showed that r-RB47 isolated from E. coli was in an active reduced form so that only a slight enhancement of RNA binding activity was obtained with addition of DTT and r-RB60.

To determine whether r-RB60 was able to re-activate r-RB47 that was in an inactive oxidized form, r-RB47 was incubated with the oxidant dithionitrobenzoic acid (DTNB) for 5 minutes and then dialyzed against $10^4$ volume of buffer to remove the oxidant. Oxidation of r-RB47 by DTNB completely abolished the binding activity of the protein. Addition of DTT to 1.0 mM partially restored the binding capacity of r-RB47, and the binding was increased three fold by the addition of up to 25 mM DTT. With increasing amounts of r-RB60, the binding activity of r-RB47 was increased compared to the samples without r-RB60 at every level of DTT tested. When DTT was not present in the incubation medium, r-RB60 alone could not restore the binding of the oxidized r-RB47 (0 mM DTT), indicating that r-RB60 requires reducing equivalents to convert the inactive oxidized form of r-RB47 to an active reduced form.

Protein disulfide isomerase is known to catalyze the formation of disulfide bonds by oxidation of the sulfhydryl groups of cysteine residues during protein folding. To examine whether r-RB60 was also capable of oxidative catalysis of the reduced form of r-RB47, GSSG, the oxidized form of the thiol tripeptide glutathionine, was added to the assay mixture. When GSSG alone was added to r-RB47 at up to 5 mM, there was a two fold reduction in binding activity of r-RB47 compared with untreated protein. Incubation of r-RB47 with both GSSG and r-RB60 reduced the binding activity of r-RB47 by 5–6 fold, indicating that r-RB60 can facilitate the conversion of the reduced form of r-RB47 to an inactive oxidized form under an oxidizing environment. Thus, RB60 modulates or in other words regulates the redox potential essential for RB47 binding activity. As such, RB60 is a regulatory protein useful in regulating the expression of a desired coding sequence in reducing and oxidizing environments as supported by the teachings described herein.

ADP-dependent phosphorylation of RB60 has previously been shown to reduce binding of the protein complex to the 5'-UTR of the psbA mRNA. To identify if recombinant RB60 can be phosphorylated, r-RB60 was incubated with heparin-purified proteins from C. reinhardtii in the presence of g-$^{32}$P-ATP. Phosphorylated r-RB60 was detected among a number of phosphorylated proteins in the heparin-purified fraction. Purification of the incubation mixtures on Ni-NTA resin resulted in the isolation of phosphorylated r-RB60. Phosphorylated r-RB60 was able to reduce the binding of r-RB47 to the 5' UTR of the psbA mRNA, whereas, phosphorylated C. reinhardtii proteins eluted from Ni-NTA resin had little impact or r-RB47 RNA binding.

It has previously been shown that thioredoxin can act as a transducer of redox potential to enhance the binding of a protein complex to the psbA mRNA. PDI fits well into this scheme as ferredoxin-thioredoxin reductase is capable of directly reducing PDI.

In a functional model of RB60 regulation, reducing equivalents, generated by photosynthesis, are donated to cPDI (RB60) through ferredoxin and ferredoxin-thioredoxin reductase and act to catalyze the reduction of chloroplast poly(A) binding protein (cPABP) (RB47). The reduced form of cPABP is then capable of binding to the 5' UTR of the psbA mRNA to activate translation initiation of this mRNA resulting in increased synthesis of the D1 protein. This mechanism provides a direct link in the chloroplast between the quantity of absorbed light and the rate of synthesis of the D1 protein, allowing the replacement of the photo-damaged D1 protein. Protein disulfide isomerase has an additional advantage in this scheme in that it has greater oxidation potential than thioredoxin, thus allowing the off switch (oxidation) when reducing potential is low. ADP-dependent phosphorylation of RB60, that might be triggered by the increased pool of ADP during dark growth, can act to reduce the RNA binding activity of cPABP by enhancing the oxidative catalysts of cPDI over the reductive catalysis, resulting in decreased translation of the psbA mRNA. The data presented here show that a PDI such as RB60 acts as a regulator of RNA binding activity and hence gene expression, and not just as a catalyst for protein folding.

The present invention therefore describes the use of a protein disulfide isomerase, such as RB60, to function as a regulator of the binding of a RB47 binding polypeptide to the RB47 binding site nucleotide sequence for the activation of translation. Thus, in view of the foregoing disclosure, the use of a protein disulfide isomerase such as RB60 has many applicabilities in the context of the present invention, particularly ensuring translational control mechanisms for expression of a desired coding sequence and production of the encoded molecule in both oxidizing and reducing environments.

Based on the translational activation mediated through the binding of an RB47 binding site sequence, typically a mRNA sequence and the regulation by the additional element of translational regulator, the present elements of RB47 binding site, an RB47 binding site polypeptide and a RB60 or like molecule are therefore referred to as a regulated translational activation system.

While the invention contemplates the use of any molecule that binds to RB47 binding site and any molecule that functions in accordance to the biological role of RB60 as described herein, in a preferred embodiments, the translational activator protein of RB47 binding site is RB47 and the translation regulatory molecule that regulates the binding of an activator to an RB47 binding site is RB60.

Preferably, a polypeptide that the regulates the binding of a separate polypeptide that binds to a RB47 binding site is present endogenously, i.e., naturally occurring, in a cell such that activation and regulation of translation mediated through a RB47 binding site occurs through an interaction of an endogenous protein with an exogenously provided RB47 binding site sequence as further described in Section C below and in the Examples. Functional RB60 protein is found endogenously found in plant chloroplasts as reviewed above.

In other embodiments, RB60 is a recombinant protein produced through the expression of the coding sequence in a recipient cell as discussed in Section C below. Expression of a recombinant RB60 is now possible in view of the cloning of the cDNA encoding of RB60 as described in the present invention and in Examples 2 and 3. An exemplary recombinant RB60 protein produced by the methods of this invention is more completely described in the Examples.

Thus, although the preferred RB60 protein and nucleic acid compositions are derived from *Chlamydomonas reinhardtii* as discussed in the present invention, variations at both the amino acid and nucleotide sequence level may exist in similar functioning molecules isolated from different algae species as well as within differing plant geni. Such variations are not to be construed as limiting as previously discussed for RB47 compositions.

C. Recombinant DNA Molecules and Expression Systems that Utilize the RB47 Binding Site The invention describes several nucleotide sequences of particular use in the methods of controlling gene expression using the RB47 binding site. These sequences include the actual RB47 binding site, the sequences which encode the RB47 protein that binds to the RB47 binding site, the RB60 protein which regulates the activity of RB47 protein, and various DNA segments, recombinant DNA (rDNA) molecules and vectors constructed for expression of these protein or for using these proteins to control expression of preselected structural genes.

DNA segments of this invention therefore can comprise sequences which encode whole structural genes, fragments of structural genes, and transcription units as described further herein.

A preferred DNA segment is a nucleotide sequence which defines an RB47 binding site as defined herein, which defines an RB47 protein, RB47 polypeptide or biologically active fragment thereof, or which defines an RB60 protein, RB60 polypeptide or biologically active fragment thereof.

The amino acid residue sequence of RB47 and of RB60 are described herein and in the Examples.

A preferred DNA segment codes for an amino acid residue sequence substantially the same as, and preferably consisting essentially of, an amino acid residue sequence or portions thereof corresponding to the RB47 or RB60 protein described herein. Representative and preferred DNA segments are further described in the Examples.

The amino acid residue sequence of a protein or polypeptide is directly related via the genetic code to the deoxyribonucleic acid (DNA) sequence of the structural gene that codes for the protein. Thus, a structural gene or DNA segment can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

A nucleic acid is any polynucleotide or nucleic acid fragment, whether it be a polyribonucleotide of polydeoxyribonucleotide, i.e., RNA or DNA, or analogs thereof. In preferred embodiments, a nucleic acid molecule is in the form of a segment of duplex DNA, i.e, a DNA segment, although for certain molecular biological methodologies, single-stranded DNA or RNA is preferred.

DNA segments are produced by a number of means including chemical synthesis methods and recombinant approaches, preferably by cloning or by polymerase chain reaction (PCR). DNA segments that encode portions of an RB47 or RB60 protein can easily be synthesized by chemical techniques, for example, the phosphotriester method of Matteucci et al, *J. Am. Chem. Soc.*, 103:3185–3191, 1981, or using automated synthesis methods. In addition, larger DNA segments can readily be prepared by well known methods, such as synthesis of a group of oligonucleotides that define the DNA segment, followed by hybridization and ligation of oligonucleotides to build the complete segment. Alternative methods include isolation of a preferred DNA segment by PCR with a pair of oligonucleotide primers.

Of course, through chemical synthesis, any desired modifications can be made simply by substituting the appropriate bases for those encoding the native amino acid residue sequence.

Furthermore, DNA segments consisting essentially of structural genes encoding an RB47 or RB60 protein can be subsequently modified, as by site-directed or random mutagenesis, to introduce any desired substitutions.

1. Cloning RB47 and RB60 Genes

An RB47 or RB60 gene of this invention can be cloned by a variety of cloning methods using *Chlamydomonas reinhardtii* (*C. reinhardtii*) as a source of the genomic DNA or messenger RNA (mRNA) for cloning purposes. Cloning these genes can be conducted according to the general methods described in the Examples.

Preferred cloning strategies for isolating a nucleic acid molecule that encodes an RB47 or RB60 protein of this invention are described in the Examples.

Sources of libraries for cloning an RB47 or RB60 gene of this invention can include genomic DNA or messenger RNA (mRNA) in the form of a cDNA library from a tissue believed to express these proteins. The preferred tissue is plant chloroplast from *C. reinhardtii*.

A preferred cloning method involves the preparation a *C. reinhardtii* chloroplast cDNA library using standard methods, and preparing the RB47 or RB60-encoding nucleotide sequence using PCR with oligonucleotide primers based on the nucleotide sequences described herein for the RB47 or RB60 genes, respectively. Alternatively, the desired cDNA clones can be identified and isolated from a cDNA or genomic library by conventional hybridization methods using a hybridization probe based on the sequences described herein. Other methods are readily apparent to one skilled in the art.

2. Expression Vectors

In addition, the invention contemplates a recombinant DNA molecule (rDNA) containing a DNA segment of this invention encoding an RB47 or RB60 protein as described herein. A rDNA can be produced by operatively (operably) linking a vector to a DNA segment of the present invention.

As used herein, the term "vector" refers to a DNA molecule capable of autonomous replication in a cell and to which another DNA segment can be operatively linked so as to bring about replication of the attached segment. A vector adapted for expression of a gene product and capable of directing the expression of a structural gene is referred to herein as an "expression vector". Thus, a recombinant DNA molecule is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of a structural gene included in DNA segments to which it is operatively linked.

Both prokaryotic and eukaryotic expression vectors are familiar to one of ordinary skill in the art of vector construction and are described by Ausebel, et al., In Current Protocols in Molecular Biology, Wiley and Sons, New York (1993) and by Sambrook et al., Molecular Cloning: A Laboratory Manual, Cold Spring Harbor Laboratory, (1989), which reference also describes all the general recombinant DNA methods referred to herein.

In one embodiment, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of a structural gene in a bacterial host cell, such as *E. coli*, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.), pRSET available from Invitrogen (San Diego, Calif.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (international Biotechnologies, Inc.), pTDT1 (ATCC, #31255), pRc/CMV (Invitrogen, Inc.), the preferred vector pcDNA3 (Invitrogen) described in the Examples, and the like eucaryotic expression vectors.

An alternative expression system that can be used to express a protein of the invention is an insect system. In one such system., Autographa californica nuclear polyhidrosis virus (AcNPV) is used as a vector to express foreign genes. The virus grows in *Spodoptera frugiperda* cells. The polypeptide-encoding nucleotide sequence may be cloned into non-essential regions (in *Spodoptera frugiperda* for example the polyhedron gene) of the virus and placed under control of an AcNPV promoter (for example the polyhedron promoter). Successful insertion of the polypeptide-encoding nucleotide sequence inactivates the polyhedron gene and production of non-occluded recombinant virus (i.e., virus lacking the proteinaceous coat coded for by the polyhedron gene). These recombinant viruses are then used to infect cells in which the inserted gene is expressed. See Smith et al., *J. Biol. Chem.*, 46:584 (1983); and Smith, U.S. Pat. No. 4,215,051.

Mammalian cell systems that utilize recombinant viruses or viral elements to direct expression may be engineered. For example, when using adenovirus expression vectors, the coding sequence of a polypeptide may be ligated to an adenovirus transcription/translation control complex, e.g., the late promoter and tripartite leader sequence. This chimeric gene may then be inserted into the adenovirus genome by in vitro or in vivo recombination. Insertion in a non-essential region of the viral genome (e.g., region E1 or E3) will result in a recombinant virus that is viable and capable of expressing the polypeptide in infected hosts (e.g., see Logan et al., *Proc. Natl. Acad. Sci., USA*, 81:3655–3659 (1984)). Alternatively, the vaccinia virus 7.5K promoter may be used. (e.g., see, Mackett et al., *Proc. Natl. Acad. Sci., USA*, 79:7415–7419 (1982); Mackett et al., *J. Virol.*, 49:857–864 (1984); Panicali et al., *Proc Natl. Acad. Sci., USA*, 79:4927–4931 (1982)). Of particular interest are vectors based on bovine papilloma virus which have the ability to replicate as extrachromosomal elements (Sarver et al., *Mol. Cell. Biol.*, 1:486 (1981)). Shortly after entry of this DNA into mouse cells, the plasmid replicates go about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the polypeptide-encoding nucleotide sequence in host cells (Cone et al., *Proc. Natl. Acad. Sci., USA*, 81:6349–6353 (1984)). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with a cDNA controlled by appropriate expression control elements (e.g., promoter and enhancer sequences, transcription terminators, polyadenylation sites, etc.), and a selectable marker. As mentioned above, the selectable marker in the recombinant plasmid confers resistance to the selection and allows cells to stably integrate the plasmid into their chromosomes and grow to form foci which in turn can be cloned and expanded into cell lines.

For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler et al., *Cell*, 11:223 (1977)), hypoxanthine-guanine phosphoribosyltransferase (Szybalska et al, *Proc. Natl. Acad. Sci., USA*, 48:2026 (1962)), and adenine phosphoribosyltransferase (Lowy et al., *Cell*, 22:817 (1980)) genes, which can be employed in tk$^-$, hgprt$^-$ or aprt$^-$ cells respectively. Also, antimetabolite resistance-conferring genes can be used as the basis of selection; for example, the genes for dhfr, which confers resistance to methotrexate (Wigler et al., *Proc. Natl. Acad. Sci., USA*, 77:3567 (1980); O'Hare et al., *Proc. Natl. Acad. Sci., USA*, 78:1527 (1981); gpt, which confers resistance to mycophenolic acid (Mulligan et al, *Proc. Natl. Acad. Sci., USA*, 78:2072, (1981)); neo, which confers resistance to the aminoglycoside G-418 (Colberre-Garapin et al, *J. Mol. Biol.*, 150:1 (1981)); and hygro, which confers resistance to hygromycin (Santerre et al, *Gene*, 30:147 (1984)). Recently, additional selectable genes have beer. described, namely trpB, which allows cells to utilize indole in place of tryptophan; hisD, which allows cells to utilize histinol in place of histidine (Hartman et al, *Proc, Natl. Acad. Sci., USA*, 85:804 (1988)); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory ed., (1987)).

In another preferred embodiment, expression vectors compatible for use with plant cells are used to express structural genes in plants. Plants provide advantageous expression and delivery aspects in that a large supply of bulk protein with universal access is readily made from which the protein is either isolatable therefrom. Thus, transgenic plants containing expression vectors for encoding a recombinant protein of this invention is useful for preparing polypeptides of this invention.

Typical expression vectors useful for expression of genes in plants are well known in the art. Typical methods for introducing genes via expression vectors into plants include *Agrobacterium tumefaciens*-mediated transformation, plant virus transfection, protoplast transformation, gene transfer into pollen, injection into reproductive organs, injection into immature embryos, and direct insertion, a process referred to as "biolystics". In the case of infection by plant viruses, a recombinant protein can be produced at high concentrations and isolated at low cost, with the genetic stocks being easily maintained for long periods of time without passaging through plants.

Preferred plants for such expression include any plant for which a compatible expression vector system exists, including dicots and monocots. Particularly preferred plants include alfalfa, tomato, petunia, soy bean, tobacco, corn, wheat, rice, spinach, asparagus, and the like. Exemplary plant expression vector systems for expression of a recombinant protein of this invention include those, such as binary vector system utilizing *Agrobacterium tumefaciens*, described in U.S. Pat. No. 5,202,422 and An et al., *Plant Molecular Biology Manual*, A3:1–19 (1988). Additional plant expression systems are described in U.S. Pat. No. 5,234,834, the disclosures of which several teachings are hereby incorporated by reference.

D. Methods

The present invention provides for a variety of methods using the disclosed recombinant proteins, nucleotide sequences, expression cassettes and expression systems. In particular, the invention provides methods for preparing (expressing) an RB47 or RB60 protein using the expression systems, methods for controlling (regulating) the expression of a preselected coding sequence using the translation regulation properties of the RB47 system, methods for screening for useful agents which affect the ability of RB47 and/or RB60 to regulate translation in these systems, and the like methods.

1. Methods for Precaring a Recombinant Protein

An RB47 OR RB60 protein of this invention can be prepared by a variety of means, although expression iusing a rDNA expression vector is preferred. Exemplary production methods for a recombinant protein are described in the Examples.

In one embodiment, the invention contemplates methods for the preparation of a recombinant RB47 or RB60 proteins in their various forms using a nucleotide sequence-based expression system. The produced proteins are useful in the various embodiments described herein.

Although the description of expression is limited to specific examples, it is to be understood that the expression of proteins is generally characterized, and the expression of, for example, full length RB47 protein serves as an example of expression of any of a variety, of forms of RB47 protein, including mature RB47, processed forms of RB47, biologically active fragments of RB47, fusion proteins containing RB47 domains, and the like. The descriptions herein apply to various forms of RB60 as well.

The method of preparing a recombinant RB47 or RB60 protein comprises providing an expression cassette as described herein that contains nucleotide sequences that encode an RB47 or RB60 protein, or fragment thereof, together with nucleotide sequences that provide the requisite information for controlling gene expression and translation. The provided cassette is introduced into a suitable expression medium and maintained under conditions and for a time period sufficient for expression and translation of the protein product to occur. The times and conditions can vary, as is well known, depending upon the expression/translation medium (e.g., intracellular medium, in vitro expression medium, etc.). Nucleotide sequence information required for expression and translation are also well known in the art and need not be described in detail herein.

A typical expression system is described herein, in which the expression cassette is present on a recombinant plasmid that has been introduced into a microbial host. For example, the expression cassette is present in a PET expression plasmid introduced into *E. coli*, and the transformed bacterial is cultivated under growth conditions suitable for growth and expression of the expression cassette. Additional expression systems include other species of bacterial cells, yeast and eucaryotic cells, including mammalian cell expression systems, and in vitro expression systems, as are well known.

After expression, the expressed RB60 or RB47 protein is readily isolated from the expression medium (i.e., the host cell and cell contents) using standard biochemical separation methods to produce an isolated recombinant protein. Typical isolation methods can include disruption of the cell followed by protein fractionations using mechanical, chemical, biological or immunological properties of the RB47 or RB60 protein. Preferred separation/isolation methods are described in the Examples.

Thus, the invention also provides a method for the production of recombinant proteins, either as intact RB47 or RB60 protein, as fusion proteins or as smaller polypeptide fragments of RB47 or RB60. The production method generally involves inducing cells to express a recombinant protein of this invention, recovering the expressed protein from the resulting cells, and purifying the expressed protein so recovered by biochemical fractionation methods, using a specific antibody of this invention, or other chemical procedures. Inducing expression of a recombinant protein can comprise inserting a rDNA vector encoding an RB47 or RB60 protein, or fragment thereof, of this invention, which rDNA is capable of expressing the structural gene encoding the RB47 or RB60 protein, into a suitable host cell, and expressing the vector's structural gene.

Thus, to facilitate expression of a recombinant protein or fusion protein of the present invention, DNA segments encoding either RB47 or RB60 as described herein, or portions thereof, are inserted into an expression vector. DNA segments are characterized as including a DNA sequence that encodes a recombinant protein of this invention, i.e., RB47 or RB60. That is, the DNA segments of the present invention are characterized by the presence of some or all of an RB47 or RB60 structural gene as described herein. Preferably the gene is present as an uninterrupted linear series of codons where each codon codes for an amino acid residue found in the native protein, i.e., a gene free of introns.

2. Translational Regulation of Expression of a Coding Sequence

In a related embodiment, the invention contemplates methods for the controlled expression of a preselected coding sequence under the regulation of RB47 or a combination of RB47 and RB60 using the nucleotide sequences described herein that define an RB47 binding site and the recombinant proteins which bind this binding site and regulate translation of adjacent nucleotide sequences.

Thus, for example, the RB47 binding site can be engineered into an expression cassette as described herein to control the expression of a structural gene nucleotide sequence which encodes a preselected gene. The expression cassette contains the following genetic elements: (1) a promoter sequence that initiates transcription of a gene, (2) an RB47 binding site sequence adjacent to and located 3' relative to the promoter sequence, (3) a structural protein coding sequence under the expression control of the promoter, and a source of RB47 protein to regulate the expression of the cassette.

The promoter can be any of a variety of genetic elements as are well known for promotion of gene transcription. The promoter can be constitutive, inducible or repressible, thereby providing further regulation. A preferred promoter is the lac z promoter inducible by IPTG, as is well known. Additional promoters include the T3 or T7 promoter.

The RB47 protein can be provided exogenously, as by addition of isolated protein to an expression medium containing the cassette, provided endogenously, as by introducing the cassette into a host cell which contains endogenous RB47 (e.g., a chloroplast cell that expresses RB47) or provided by introducing a gene which expresses the RB47 protein into the expression medium, either in combination with the cassette, or substantially contemporaneously with the cassette. The RB47 encoding gene can be added as a separate plasmid, or can be present as a second translation unit on the cassette which expresses the preselected gene.

Thus, in one embodiment, the invention comprises first forming an expression cassette by operably linking the above-identified components, and then introducing the expression cassette into a cell or other suitable expression medium.

Where the expression system can be further regulated by RB60, the RB60 protein can be added to the expression system exogenously from purified recombinant protein, provided as an endogenous protein when expression is carried out in a plant cell, or can be provided by expression from a second translation unit. The second transcription unit can be present on a separate nucleotide sequence, such as a separate plasmid capable of expressing RB60 that contains the RB60 nucleotide sequence, or present on the same expression cassette as a separate translation unit for RB60.

Expression cassettes can be introduced into an expression medium by any of a variety of means, and therefore the invention need not be so limited. For example, a variety of cell types can be used including bacterial, plant, yeast and higher eukaryote, all of which have different methods for transformation, including transduction, transfection, electroporation, transformation, biolistic bombardment, infection, and the like.

These systems provide particular advantages in the expression of preselected genes, including structural genes, insofar as these systems provide the ability to control timing and amounts of expression by specific and strong regulators of translation. The advantages will be apparent to one skilled in the art, but include synchronized expression in cell populations, combining expression with nutrient supplementation, regulated expression in therapeutic, manufacturing and diagnostic expression applications, and the like systems.

In one embodiment, the method for expression of a desired (preselected) coding sequence comprises first the method of preparing an expression cassette having the various components described herein, followed by introducing the cassette into an expression medium and maintaining the cassette under condition suitable for expression. To that end, the cassette can be prepared by any recombinant DNA method, which methods are well established in the art, including use of restriction enzymes to ligate nucleotide fragments, polymerase chain reactions (PCR) to isolate, mutate, modify and manipulate nucleotide fragments, and cloning sites for insertion of preselected genes. An exemplary method involves operably linking the RB47 binding site sequence to a cloning site for insertion of a desired coding sequence, such that the cloning site is downstream of the binding site, and linking a second nucleotide sequence which encodes an RB47 polypeptide. The method can further involve linking a promoter 5' upstream to the RB47 binding site to form a transcription unit containing from 5' to 3' a promoter, a binding site and a cloning site for inserting the desired coding sequence. In a subsequent step for forming an expression cassette, the desired coding sequence is inserted into the cloning site.

Other permutations will be apparent to one skilled in the art.

3. Screening for Agonists and Antagonists of RB47-Mediated Translation

In another embodiment, the invention contemplates using an expression cassette containing an RB47 binding site to screen for agonists and antagonists which affect RB47 binding to the RB47 binding site, thereby identifying useful reagents for further control of an RB47-regulated (mediated) translation unit.

The method comprises providing an expression cassette according to the invention and having a indicator polypeptide as the desired structural gene into an expression system (i.e., medium), introducing RB47 and the candidate agent, and detecting the amount of indicator polypeptide expressed, and thereby the amount of effect the agent has on the expression system. Controls are typically run in the presence and absence of the RB47 protein to demonstrate selectivity of the agent, which could be either an agonist or antagonist of RB47 activation of translation upon binding to the RB47 binding site.

Typical indicator polypeptides include enzymes which produce detectable substrates, light producing enzymes, such as luciferase, and the like. The RB47 can be added in the form of exogenous protein or by expression off of a nucleotide sequence, as described earlier.

In one embodiment, the expression system is a cell capable of supporting expression (transcription and translation) and the RB47 is provided in the cell either by adding protein to the cell or by providing a RB47-encoding nucleotide sequence to the cell.

In a further embodiment, the screening method is useful to identify agonists or antagonists of RB60 or RB60-mediated regulation of RB47-mediated translation, ie., reagents which effect RB60 rather than RB47 directly. This embodiment requires that the additional component RB60 be included in the screening method as described herein for expression using RB60.

Additional permutations are readily apparent to one skilled in the art.

E. Articles of Manufacture

The present invention also contemplates an article of manufacture comprising one or more of the components of the present invention. Typically, the article is present in the form of a package containing the component or in combination with packaging material. The packaging material includes a label or instructions for use of the components of the package. The instructions indicate the contemplated use of the component as described herein for the methods or compositions of the invention.

For example, an article of manufacture can comprise one or both of the recombinant proteins of the invention, RB47 and RB60, in amounts useful in a method according to the invention. Alternatively, an article of manufacture can contain an expression cassette for expressing a desired coding sequence, which cassette comprises a construction as described herein that includes an RB47 binding site, and can optionally include a cloning site for insertion of a desired coding sequence, a promoter for controlling transcription of the expression cassette and inserted coding sequence, a coding sequence for the RB47 protein and/or the RB60 protein, and a preselected coding sequence. Alternatively, the article of manufacture may contain multiple nucleotide sequences, such as separate plasmid each encoding a different transcription, comprising one or more of the desired coding sequence under control of the RB47 binding site, the RB47 coding sequence and the RB60 coding sequence.

The article of manufacture may optionally include both an expression cassette and one or both of the recombinant proteins RB47 and RB60, or may contain a cell transformed by one or more of the expression cassettes of the present invention.

In a related embodiment, an expression cassette may be used for expressing an RNA transcript containing an RB47 binding site, useful for subsequent regulation of translation of the transcript by RB47 protein. Such a construct can be used in the RNA expression field. Therefore, the invention contemplates an article of manufacture comprising packaging material, and in a separate container an expression cassette for expressing RNA that includes the RB47 binding site, wherein the packaging material includes a label that indicates the uses of the cassette in producing in vitro RNA transcripts. The production of RNA transcripts is well known. The article can further contain in separate containers components useful in combination with the cassette, including polymerases buffers, ribonucleotides and other reagents for in vitro transcription.

In these permutations, the components may optionally be present in the article of manufacture in separate containers.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Cloning of RB47

RB47 protein, 47 kilodalton (kDa) was purified by published procedures (Danon and Mayfield, *Embo J.*, 10:3993–4001 (1991)). The protein was then digested with proteinase Lys-C or trypsin, and the peptides separated HPLC and microsequenced (John Lesyk, Worchester Foundation for Experimental Biology, Worcester, Mass. and Arie Admon, The Protein Center, Department of Biology, Technion, Haifa, Israel). Two peptide sequences were obtained (QYGFVHFEDQAAADR (SEQ ID NO 1) and GFGFINFKDAESAA (SEQ ID NO 2)). Degenerate oligonucleotides were designed based on the reverse translation of these peptides. For the QYG . . . and GFG . . . peptides, the respective oligonucleotide sequences were 5' CAGTACGGYTTCGTBCAYTTCGAGGAYCAGGC3' (SEQ ID NO 3) and 5'<u>GGAATTC</u>GGYTT- CGGYTTCATYAACT-TCAAGGAYGCBGAG3' (SEQ ID NO 4), where the underline indicates an Eco RI restriction site and where Y=C or T; and B=G or T or C. A *C. reinhardtii* cDNA λ-gt10 phage library obtained from EMBL Laboratories, Heidelberg, Germany, was screened with these oligonucleotides using standard methods as described by Sambrook et al., *Molecular Cloning: A Laboratory Manual*, Cold Spring Harbor Laboratory Press, Chapter 8, 1989. One set of duplicate filter lifts was probed with each oligonucleotide, and plaques that hybridized to both were isolated. Several cDNA clones that hybridized to oligonucleotides from both peptides were identified. Four of these clones were 2.6 kilobases (kb) in length, the predicted full length of the RB47 mRNA. One of these cDNAs was subcloned into an *E. coli* plasmid for sequence determination using an automated sequencer.

The nucleotide and encoded amino acid sequence of RB47 is also shown in FIGS. 1A–1D (SEQ ID NO 5). As described in Section 2 above, the predicted protein sequence from the cloned cDNA contained both the derived peptide sequences of RB47 and is highly homologous to poly(A) binding proteins (PABP) from a variety of eukaryotic organisms.

2. Cloning of R860

To clone the cDNA encoding the 60 kDa psbA mRNA binding protein (RB60), the psbA-specific RNA binding proteins were purified from light-grown *C. reinhardtii* cells using heparin-agarose chromatography followed by psbA RNA affinity chromatography (RAC). RAC-purified proteins were separated by two-dimensional polyacrylamide gel electrophoresis. The region corresponding to RB60 was isolated from the PVDF membrane. RB60 protein was then digested with trypsin. Unambiguous amino acid sequences were obtained from two peptide tryptic fragments (WFVDGELASDYNGPR (SEQ ID NO 6) and (QLILWTTADDLKADAEIMTVFR (SEQ ID NO 7)) as described above for RB47. The calculated molecular weights of the two tryptic peptides used for further analysis precisely matched with the molecular weights determine by mass spectrometry. The DNA sequence corresponding to one peptide of 22 amino acid residues was amplified by PCR using degenerate oligonucleotides, the forward primer 5'CGCGGATCCGAYGCBGAGATYATGAC3' (SEQ ID NO 8) and the reverse primer 5'CGCGAATTCGTC-ATRATCTCVGCRTC3' (SEQ ID NO 9), where R can be A or G (the other IUPAC nucleotides have been previously defined above). The amplified sequence was then used to screen a λ-gt10 cDNA library from *C. reinhardtii*. Three clones were identified with the largest being 2.2 kb. Selection and sequencing was performed as described for RB47 cDNA.

The resulting RB60 cDNA sequence is available via GenBank (Accession Number AF027727). The nucleotide and encoded amino acid sequence of RB60 is also shown in FIGS. 2A–2B (SEQ ID NO 10). The protein coding sequence of 488 amino aced residues corresponds to nucleotide positions 16–1614 of the 2413 base pair sequence. The predicted amino acid sequence of the cloned cDNA contained the complete amino acid sequences of the two tryptic peptides. The amino acid sequence of the encoded protein revealed that it has high sequence homology to both plant and mammalian protein disulfide isomerase (PDI), and contains the highly conserved thioredoxin-like domains with -CysGlyHisCys- (-CGHC-) (SEQ ID NO 11) catalytic sites in both the N-terminal and C-terminal regions and the -LysAspGluLeu- (-KDEL-) (SEQ ID NO 12) endoplasmic reticulum (ER) retention signal at the C-terminus found in all PDIs. PDI is a multifunctional protein possessing enzymatic activities for the formation, reduction, and isomerization of disulfide bonds during protein folding, and is typically found in the ER. The first 30 amino acid residues of RB60 were found to lack sequence homology with the N-terminal signal sequence of PDI from plants or mammalian cells. However, this region has characteristics of chloroplast transit peptides of *C. reinhardtii*, which have similarities with both mitochondrial and higher plant chloroplast presequences. A transit peptide sequence should override the function of the -KDEL- ER retention signal and target the protein to the chloroplast since the -KDEL- signal acts only to retain the transported protein in the ER.

3. Preparation of psbA Promoter Sequence and RB47 Binding Site Nucleotide Sequence The chloroplast psbA gene from the green unicellular alga *C. reinhardii* was cloned and sequenced as described by Erickson et al., *Embo J*., 3:2753–2762 (1984), the disclosure of which is hereby incorporated by reference. The DNA sequence of the coding regions and the 5' and 3' untranslated (UTR) flanking sequences of the *C. reinhardii* psbA gene is shown in FIGS. 3A–3C. The psbA gene sequence is also available through GenBank as further discussed in Example 4. The nucleotide sequence is also listed as SEQ ID NO 13. The deduced amino acid sequence (also listed in SEQ ID NO 13) of the coding region is shown below each codon beginning with the first methionine in the open reading frame. Indicated in the 5' non-coding sequence are a putative Shine-Dalgarno sequence in the dotted box, two putative transcription initiation sites determined by S1 mapping (S1) and the Pribnow-10 sequence in the closed box. Inverted repeats of eight or more base pairs are marked with arrows and labeled A–D. A direct repeat of 3' base pairs with only two mismatches is marked with arrows labeled 3'. Indicated in the 3' non-coding sequence is a large inverted repeat marked by a forward arrow and the S1 cleavage site marking the 3' end of the mRNA. Both the 5' and 3' untranslated regions are used in preparing one of the expression cassettes of this invention as further described below.

The 5' UTR as previously discussed contains both the psbA promoter and the RB47 binding site. The nucleotide sequence defining the psbA promoter contains the region of the psbA DNA involved in binding of RNA polymerase to initiate transcription. The –10 sequence component of the psbA promoter is indicated by the boxed nucleotide sequence upstream of the first S1 while the –35 sequence is located approximately 35 bases before the putative initiation site. As shown in FIG. 3, the –10 sequence is boxed, above which is the nucleotide position (–100) from the first translated codon. The –35 sequence is determined accordingly. A psbA promoter for use in an expression cassette of this invention ends at the first indicated S1 site (nucleotide position –92 as counting from the first ATG) in FIG. 3 and extends to the 5' end (nucleotide position –251 as shown in FIG. 3). Thus, the promoter region is 160 bases in length. A more preferred promoter region extends at least 100 nucleotides to the S1 end from the S1 site. A most preferred region contains nucleotide sequence ending at the S1 site and extending 5' to include the –35 sequence, i.e., from –92 to –130 as counted from the first encoded amino acid residue (39 bases).

The psbA RB47 binding site region begins at the first S1 site as shown in FIG. 3 and extends to the first adenine base of the first encoded methionine residue. Thus, a psbA RB47 binding site in the psbA gene corresponds to the nucleotide positions from –91 to –1 as shown in FIG. 3.

The above-identified regions are used to prepare expression constructs as described below. The promoter and RB47 binding site regions can be used separately; for example, the RB47 binding site sequence can be isolated and used in a eukaryotic or prokaryotic plasmid with a non-psbA promoter. Alternatively, the entire psbA 5' UTR having 251 nucleotides as shown in FIG. 3 is used for the regulatory region in an expression cassette containing both the psbA promoter and RB47 binding site sequence as described below.

4. Preparation of Expression Vectors and Expression of Coding Sequences

A. Constructs Containing an psbA Promoter, an RB47 Binding Site Nucleotide Sequence, a Desired Heterologous Coding Sequence, an RB47-Encoding Sequence and an RB60-Encoding Sequence Plasmid expression vector constructs, alternatively called plasmids, vectors, constructs and the like, are constructed containing various combinations of elements of the present invention as described in the following examples. Variations of the positioning and operably linking of the genetic elements described in the present invention and in the examples below are contemplated for use in practicing the methods of this invention. Methods for manipulating DNA elements into operable expression cassettes are well known in the art of molecular biology. Accordingly, variations of control elements, such as constitutive or inducible promoters, with respect to prokaryotic or eukaryotic expression systems as described in Section C. are contemplated herein although not enumerated. Moreover, the expression the various elements is not limited to one transcript producing one mRNA; the invention contemplates protein expression from more than one transcript if desired.

As such, while the examples below recite one or two types of expression cassettes, the genetic elements of RB47 binding site, any desired coding sequence, in combination with RB47 and RB60 coding sequences along with a promoter are readily combined in a number of operably linked permeations depending on the requirements of the cell system seiected for the expression. For example, for expression in a chloroplast, endogenous RB47 protein is present therefore an expression cassette having an RB47 binding site and a desired coding sequence is minimally required along with an operative promoter sequence. Overexpression of RB47 may be preferable to enhance the translation of the coding sequence; in that case, the chloroplast is further transformed with an expression cassette containing an RB47-encoding sequence. Although the examples herein and below utilize primarily the sequence encoding the precursor form of RB47, any of the RB47-encoding sequences described in the present invention, i.e., RB47 precursor, mature RB47 and histidine-modified RB47 are contemplated for use in any expression cassette and system as described herein. To regulate the activation of translation, an RB60-encoding element is provided to the expression system to provide the ability to regulate redox potential in the cell as taught in Section B. These examples herein and below represent a few of the possible permutations of genetic elements for expression in the methods of this invention.

In one embodiment, a plasmid is constructed containing an RB47 binding site directly upstream of an inserted coding region for a heterologous protein of interest, and the RB47 and RB60 coding regions. Heterologous refers to the nature of the coding region being dissimilar and not from the same gene as the regulatory molecules in the plasmid, such as RB47 and RB60. Thus, all the genetic elements of the present invention are produced in one transcript from the IPTG-inducible psbA promoter. Alternative promoters are similarly acceptable.

The final construct described herein for use in a prokaryotic expression system makes a single mRNA from which all three proteins are translated. The starting plasmid is any *E. coli* based plasmid containing an origin of replication and selectable marker gene. For this example, the Bluescrint plasmid, pBS, commercially available through Stratagene, Inc., La Jolla, Calif., which contains a polylinker-cloning site and an ampicilin resistant marker is selected for the vector.

The wild-type or native psbA gene (Erickson et al., *Embo J.*, 3:2753–2762 (1984), also shown in FIG. 3, is cloned into pBS at the EcoRI and BamHI sites of the polylinker. The nucleotide sequence of the psbA gene is available on GenBank with the 5' UTR and 3' UTR respectively listed in Accession Numbers X01424 and X02350. The EcoRI site of psbA is 1.5 kb upstream of the psbA initiation codon and the BamHI site is 2 kb downstream of the stop codon. This plasmid is referred to as pDl.

Using site-directed PCR mutagenesis, well known to one of ordinary skill in the art, an NdeI site is placed at the initiation codon of psbA in the pDl plasmid so that the ATG of the NdeI restriction site is the ATG initiation codon. This plasmid is referred to as pDl/Nde. An Nde site is then placed at the initiation codon of the gene encoding the heterologous protein of interest and an Xho I site is placed directly downstream (within 10 nucleotides) of the TAA stop codon of the heterologous protein coding sequence. Again using site-directed mutagenesis, an XhoI site is placed within 10 nucleotides of the initiation codon of RB47, the preparation of which is described in Example 2, and an NotI site is placed directly downstream of the stop codon of RB47. The heterologous coding region and the RB47 gene are then ligated into pDl/Nde so that the heterologous protein gene is directly adjacent to the RB47 binding site and the RB47 coding region is downstream of the heterologous coding region, using the Xho I site at the heterologous stop codon and the Not I site of the pDl polylinker.

These genetic manipulations result in a plasmid containing the 5' end of the psbA gene including the promoter region and with the RB47 binding site immediately upstream of a heterologous coding region, and the RB47 coding region immediately downstream of the heterologous coding region. The nucleotides between the stop codon of the heterologous coding region and the initiation codon of the RB47 coding region is preferably less than 20 nucleotides and preferably does not contain any additional stop codons in any reading frame. This plasmid is referred to as pD1/RB47.

Figure 4:
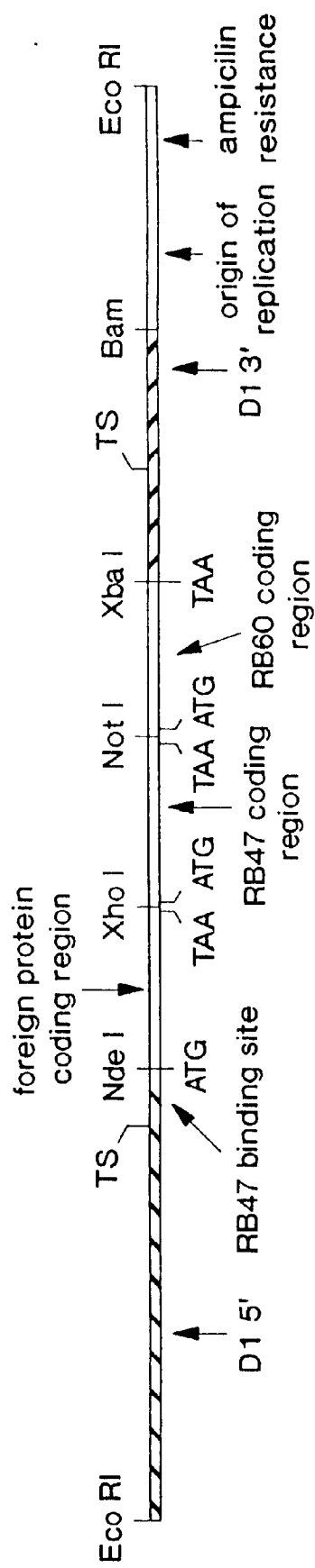
FIG. 4 is a schematic diagram of an expression cassette containing on one transcription unit from 5' to 3', a promoter region derived from the psbA gene for encoding the D1 protein from *C. reinhardtii* further containing a transcription initiation site (TS), the RB47 binding site, a region for insertion of a foreign or heterologous coding region, a RB47 coding region, a RB60 coding region, and the 3' flanking region containing transcription termination site (TS), flanked by an origin of replication and selection marker. Restriction endonuclease sites for facilitating insertion of the independent genetic elements are indicated and further described in Example 4A.

Using site-directed mutagenesis, a NotI site is placed immediately (within 10 nucleotides) upstream of the initiation codon of RB60, the preparation of which is described in Example 2, and an Xba I site is placed downstream of the RB60 stop codon. This DNA fragment is then ligated to the 3' end of the psbA gene using the Xba I site found in the 3' end of the psbA gene so that the psbA 3' end is downstream of the RB60 coding region. This fragment is then ligated into the pD1/RB47 plasmid using the NotI and BamHI sites so that the RB60 coding region directly follows the RB47 coding region. The resulting plasmid is designated pD1/RB47/RB60. Preferably there is less then 20 nucleotides between the RB47 and RB60 coding regions and preferably there are no stop codons in any reading frame in that region. The final plasmid thus contains the following genetic elements operably linked in the 5' to 3' direction: the 5' end of the psbA gene with a promoter capable of directing transcription in chloroplasts, an RB47 binding site, a desired heterologous coding region, the RB47 coding region, the RB60 coding region, and the 3' end of the psbA gene which contains a transcription termination and mRNA processing site, and an *E. coli* origin of replication and amplicillin resistance gene. A diagram of this plasmid with the restriction sites is shown in FIG. 4.

Expression of pD1/RB47/RB60 in *E. coli* to produce recombinant RB47, RB60 and the recombinant heterologous protein is performed as described in Example 4B. The heterologous protein is then purified as further described.

Expression cassettes in which the sequences encoding RB47 and RB60 are similarly operably linked to a heterologous coding sequence having the psbA RB47 binding site as described in Example 3 are prepared with a different promoter for use in eukaryotic, such as mammalian expression systems. In this aspect, the cassette is similarly prepared as described above with the exception that restriction cloning sites are dependent upon the available multiple cloning sites in the recipient vector. Thus, the RB47 binding site prepared in Example 3 is prepared for directed ligation into a selected expression vector downstream of the promoter in that vector. The RB47 and RB60 coding sequences are obtained from the pD1/RB47/RB60 plasmid by digestion with XhoI and XbaI and inserted into a similarly digested vector if the sites are present. Alternatively, site-directed mutagenesis is utilized to create appropriate linkers. A desired heterologous coding sequence is similarly ligated into the vector for expression.

B. Constructs Containing RB47 Nucleotide Sequence

1) Purified Recombinant RB47 Protein

In one approach to obtain purified recombinant RB47 protein, the full length RB47 cDNA prepared above was cloned into the *E. coli* expression vector pET3A (Studier et al., *Methods Enzymol.*, 185:60–89 (1990)), also commercially available by Novagen, Inc., Madison, Wis. and transformed into BL21 *E. coli* cells. The cells were grown to a density of 0.4 ($OD_{600}$), then induced with 0.5 mM IPTG. Cells were then allowed to grow for an additional 4 hours, at which point they were pelleted and frozen.

Confirmation of the identity of the cloned cDNA as encoding the authentic RB47 protein was accomplished by examining protein expressed from the cDNA by immunoblot analysis and by RNA binding activity assay. The recombinant RB47 protein produced when the RB47 cDNA was expressed was recognized by antisera raised against the *C. reinhardtii* RB47 protein. The *E. coli* expressed protein migrated at 80 kDa on SDS-PAGE, but the protein was actually 69 kDa, as determined by mass spectrometry of the *E. coli* expressed protein. This mass agrees with the mass predicted from the cDNA sequence. A 60 kDa product was also produced in *E. coli*, and recognized by the antisera against the *C. reinhardtii* protein, which is most likely a degradation or early termination product of the RB47 cDNA. The recombinant RB47 protein expressed from the RB47 cDNA is recognized by the antisera raised against the *C. reinhardtii* protein at levels similar to the recognition of the authentic *C. reinhardtii* RB47 protein, demonstrating that the cloned cDNA produces a protein product that is immunologically related to the naturally produced RB47 protein. In order to generate a recombinant equivalent of the endogenous native RB47, the location of the 47 kDa polypeptide was mapped on the full-length recombinant protein by comparing mass spectrometric data of tryptic digests of the *C. reinhardtii* 47 kDa protein and the full-length recombinant protein. Thus, peptide mapping by mass spectrometry has shown that the endogenous RB47 protein corresponds primarily to the RNA binding domains contained within the N-terminal region of the predicted precursor protein, suggesting that a cleavage event is necessary to produce the mature 47 kDa protein. Thus, full-lenath recombinant RB47 is 69 kDa and contains a carboxy domain that is cleaved in vivo to generate the endogenous mature form of RB47 that is 47 kDa.

To determine if the heterologously expressed RB47 protein was capable of binding the psbA RNA, the *E. coli* expressed protein was purified by heparin agarose chromatography. The recombinant RB47 protein expressed in *E. coli* was purified using a protocol similar to that used previously for purification of RB47 from *C. reinhardtii*. Approximately 5 g of *E. coli* cells grown as described above were resuspended in low salt extraction buffer (10 mM Tris [pH 7.5], 10 mM NaCl, 10 mM $MgCl_2$, 5 mM β-mercaptoethanol) and disrupted by sonication. The soluble cell extract was applied to a 5 mL Econo-Pac heparin cartridge (Bio-Rad) which was washed prior to elution of the RB47 protein (Danon and Mayfield, *Embo J.*, 10:3993–4001 (1991)).

The *E. coli* expressed protein that bound to the heparin agarose matrix was eluted from the column at the same salt concentration as used to elute the authentic *C. reinhardtii* RB47 protein. This protein fraction was used in in vitro binding assays with the psbA 5' UTR. Both the 69 and 60 kDa *E. coli* expressed proteins crosslinked to the radiolabeled psbA 5' UTR at levels similar to crosslinking of the endogenous RB47 protein, when the RNA/protein complex is subjected to UV irradiation.

Heparin agarose purified proteins, both from the *E. coli* expressed RB47 cDNA and from *C. reinhardtii* cells, were used in an RNA gel mobility shift assay to determine the relative affinity and specificity of these proteins for the 5' UTR of the psbA mRNA. The *E. coli* expressed proteins bound to the psbA 5' UTR in vitro with properties that are similar to those of the endogenous RB47 protein purified from *C. reinhardtii*. RNA binding to both the *E. coli* expressed and the enaogenous RB47 protein was competed using either 200 fold excess of unlabeled psbA RNA or 200 fold excess of poly(A) RNA. RNA binding to either of these proteins was poorly competed using 200 fold excess of total RNA or 200 fold excess of the 5' UTR of the psbD or psbC RNAs. Different forms of the RB47 protein (47 kDa endogenous protein vs. the 69 kDa *E. coli* expressed protein) may account for the slight differences in mobility observed when comparing the binding profiles of purified *C. reinhardtii* protein to heterologously expressed RB47.

The mature form of RB47 is also produced in recombinant form by the insertion by PCR of an artificial stop codon in the RB47 cDNA at nucleotide positions 1403–1405 with a stop codon resulting in a mature RB47 recombinant protein having 402 amino acids as shown in FIG. 1. An example of this is shown in FIG. 5 for the production of a recombinant histidine-modified RB47 mature protein as described below. The complete RB47 cDNA is inserted into an expression vector, such as pET3A as described above, for expression of the mature 47 kDa form of the RB47 protein. In the absence of the inserted stop codon, the transcript reads through to nucleotide position 2066–2068 at the TAA stop codon to produce the precursor RB47 having the above-described molecular weight characteristics and 623 amino acid residues.

Recombinant RB47 is also expressed and purified in plant cells. For this aspect, *C. reinhardtii* strains were grown in complete media (Tris-acetate-phosphate [TAP] (Harris, The Chlamydonas Sourcebook, San Diego, Calif., Academic Press (1989)) to a density of $5×10^6$ cells/mL under constant light. Cells were harvested by centrifugation at 4° C. for 5 minutes at 4,000 g. Cells were either used immediately or frozen in liquid $N_2$ for storage at −70° C.

Recombinant R347 protein was also produced as a modified RB47 protein with a histidine tag at the amino-terminus according to well known expression methods using pET19-D vectors available from Novagen, Inc., Madison, Wis. The nucleotide and amino acid sequence of a recombinant histidine-modified RB47 of the mature 47 kDa form is shown in FIG. 5 with the nucleotide and amino acid sequence also fisted in SEQ ID NO 14. Thus the nucleotide sequence of a histidine-modified RB47 is 1269 bases in length. The precursor form of the RB47 protein is similarly obtained in the expression system, both of which are modified by the presence of a histidine tag that allows for purification by metal affinity chromatography.

The recombinant histidine-modified RB47 purified

The recombinant histidine-modified RB47 purified through addition of a poly-histidine tag followed by $Ni^{+2}$ column chromatography showed similar binding characteristics as that described for recombinant precursor RB47 described above.

C. Constructs Containing RB60 Nucleotide Sequence

In one approach to obtain purified recombinant RB60 protein, the full-length RB60 cDNA prepared above was cloned into the *E. coli* expression vector pET3A (Studier et al., *Methods Enzymol.*, 185:60–89 (1990)), also commercially available by Novagen, Inc., Madison, Wis. and transformed into BL21 *E. coli* cells. The cells were grown to a density of 0.4 ($OD_{600}$), then induced with 0.5 mM IPTG. Cells were then allowed to grow for an additional 4 hours, at which point they were pelleted and frozen.

Recombinant histidine-modified RB60 was also expressed with a pET19-D vector as described above for RB47 that was similarly modified. Purification of the recombinant RB60 proteins was performed as described for RB47 thereby producing recombinant RB60 proteins for use in the present invention.

The RB60 coding sequence is also mutagenized for directional ligation into an selected vector for expression in alternative systems, such as mammalian expression systems.

D. Constructs Containing an RB47-Encoding Sequence and an RB60-Encoding Sequence To prepare an expression cassette for encoding both RB47 and RB60, one approach is to digest plasmid pD1/RB47/RB60 prepared above with XhoI and XbaI to isolate the fragment for both encoding sequences. The fragment is then inserted into a similarly digested expression vector if available or is further mutagenized to prepare appropriate restriction sites.

Alternatively, the nucleotide sequences of RB47 and RB60, as described in Example 2, are separately prepared for directional ligation into a selected vector.

An additional embodiment of the present invention is to prepare an expression cassette containing the RB47 binding site along with the coding sequences for RB47 and RB60, the plasmid pD1/RB47/RB60 prepared above is digested with NdeI and XhoI to prepare an expression cassette in which any desired coding sequence having similarly restriction sites is directionally ligated. Expression vectors containing both the RB47 and RB60 encoding sequences in which the RB47 binding site sequence is utilized with a different promoter are also prepared as described in Example 4A.

E. Constructs Containing an RB47 Binding Site Nucleotide Sequence, Insertion Sites for a Desired Heterologous Coding Sequence, and an RB47-Encoding Sequence In another permutation, a plasmid or expression cassette is constructed containing an RB47 binding site directly upstream of an inserted coding region for a heterologous protein of interest, and the RB47 coding region. The final construct described herein for use in a prokaryotic expression system makes a single mRNA from which both proteins are translated.

Figure 6:
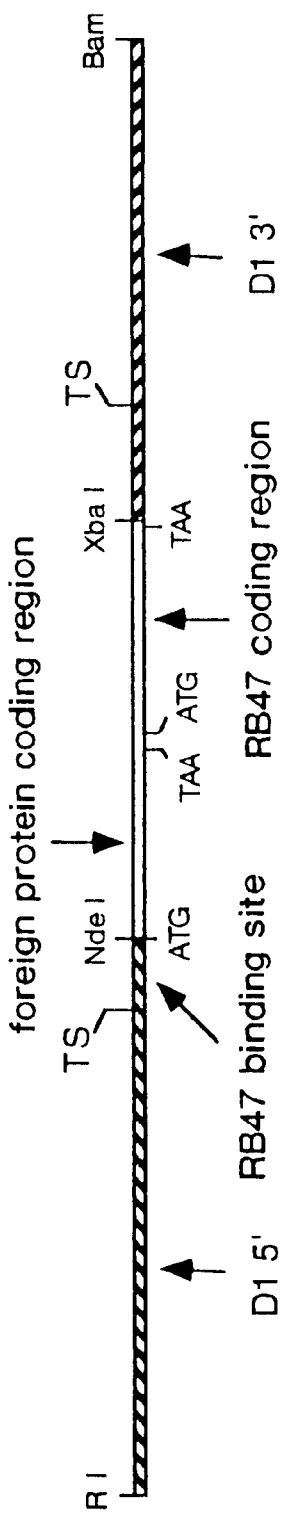
FIG. 6 is a schematic diagram of an expression cassette containing on one transcription unit from 5' to 3', a promoter region derived from the psbA gene for encoding the D1 protein from *C. reinhardtii* further containing a transcription initiation site (TS), the RB47 binding site, a region for insertion of a foreign or heterologous coding region, a RB47 coding region, and the 3' flanking region containing transcription termination site (TS). Restriction endonuclease sites for facilitating insertion of the independent genetic elements are indicated and further described in Example 4E.

The plasmid referred to as pD1/RB47 is prepared as described above in Example 4A. A diagram of this plasmid with the restriction sites is shown in FIG. 6.

Expression of pD1/RB47 in *E. coli* to produce recombinant RB47 and the recombinant heterologous protein is performed as described in above. The heterologous protein is then purified as further described.

To produce an expression cassette that allows for insertion of an alternative desired coding sequence, the plasmid pD1/RB47 is digested with NdeI and XhoI resulting in a vector having restriction endonuclease sites for insertion of a desired coding sequence operably linked to a RB47 binding site and RB47 coding sequence on one transcriptional unit.

F. Constructs Containing an RB47 Binding Site Nucleotide Sequence, Insertion Sites for a Desired Heterologous Coding Sequence, and an RB47-Encoding Sequence In another permutation, a plasmid or expression cassette is constructed containing an RB47 binding site directly upstream of an inserted coding region for a heterologous protein of interest, and the RB60 coding region. The final construct described herein for use in a prokaryotic expression system makes a single mRNA from which both proteins are translated. In this embodiment, a separate construct encoding recombinant RB47 as described in Example 4B is co-transformed into the *E. coli* host cell for expression.

The plasmid referred to as pD1/RB60 is prepared as described above for pD1/RB47 in Example 4A with the exception that XhoI and XbaI sites are created on RB60 rather than RB47.

Expression of pD1/RB60 in *E. coli* to produce recombinant RB60 and the recombinant heterologous protein is performed as described in above with the combined expression of RB47 from a separate expression cassette. The heterologous protein is then purified as further described.

To produce an expression cassette that allows for insertion of an alternative desired coding sequence, the plasmid pD1/RB60 is digested with NdeI and XhoI resulting in a vector having restriction endonuclease sites for insertion of a desired coding sequence operably linked to a RB47 binding site and RB60 coding sequence on one transcriptional unit.

G. Constructs Containing RB47 Binding Site Nucleotide Sequence and Heterologous Coding Sequences 1) Expression of Recombinant Tetanus Toxin Single Chain Antibody The examples herein describe constructs that are variations of those described above. The constructs described below contain an RB47 binding site sequence and a heterologous coding sequence. The activating protein RB47 was endogenously provided in the chloroplast and or plant cell. In other aspects however as taught by the methods of the present invention, the chloroplast is further transformed with an RB47-expression construct as described above for overexpression of RB47 to enhance translation capacities.

Figure 7:
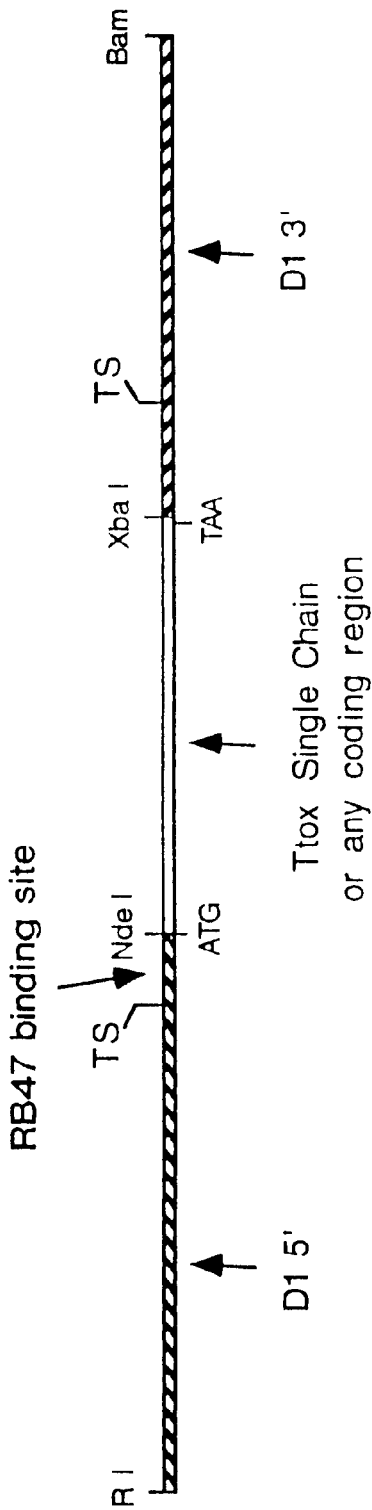
FIG. 7 is a schematic diagram of an expression cassette containing on one transcription unit from 5' to 3', a promoter region derived from the psbA gene for encoding the D3 protein from *C. reinhardtii* further containing a transcription initiation site (TS), the RB47 binding site, a region for insertion of a foreign or heterologous coding region, and the 3' flanking region containing transcription termination site (TS). Restriction endonuclease sites for facilitating insertion of the independent genetic elements are indicated and further described in Example 4G.

A strain of the green algae *Chlamydomonas reinhardtii* was designed to allow expression of a single chain antibody gene in the chloroplast. The transgenically expressed antibody was produced from a chimeric gene containing the promoter and 5' untranslated region (UTR) of the chloroplast psbA gene prepared as described above, followed by the coding region of a single chain antibody (encoding a tetanus toxin binding antibody), and then the 3' UTR of the psbA gene also prepared as described above to provide for transcription termination and RNA processing signals. This construct is essentially pD1/Nde including a heterologous coding sequence having a 3' XbaI restriction site for ligation with the 3' psbA gene and is diagramed in FIG. 7.

The psbA-single chain construct was first transformed into *C. reinhardtii* chloroplast and transformants were then screened for single chain gene integration. Transformation of chloroplast was performed via bolistic delivery as described in U.S. Pat. Nos. 5,545,818 and 5,553,878, the disclosures of which are hereby incorporated by reference. Transformation is accomplished by homologous recombination via the 5' and 3' UTR of the psbA mRNA.

Figure 8:
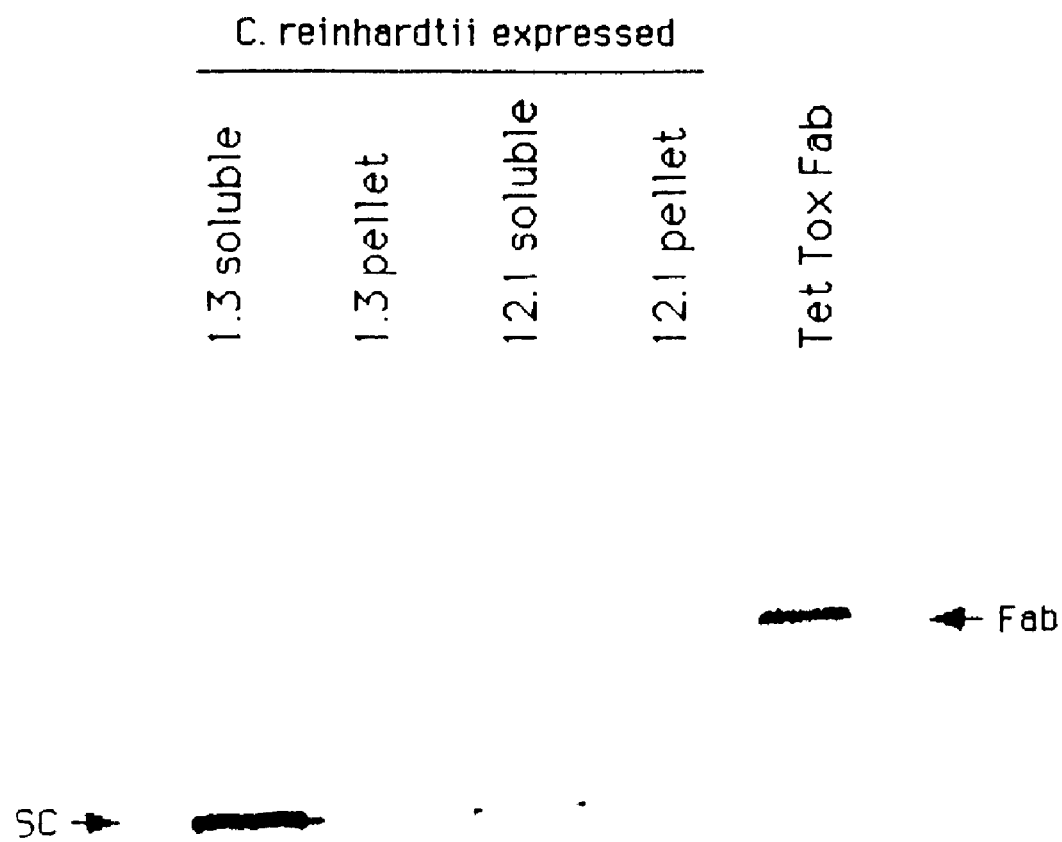
FIG. 8 is a Western blot of a tetanus toxin single chain antibody expressed with a construct of the present invention as further described in Example 4G1).

As shown in FIG. 8, two of the transformants that contained the single chain chimeric gene produced single chain antibodies at approximately 1% of total protein levels. The transgenic antibodies were of the correct size and were completely soluble, as would be expected of a correctly folded protein. Few degradation products were detectable by this Western analysis, suggesting that the proteins were fairly stable within the chloroplast. To identify if the produced antibody retained the binding capacity for tetanus toxin, ELISA assays were performed using a mouse-produced Fab, from the original tetanus toxin antibody, as the control. The chloroplast single chain antibody bound tetanus toxin at levels similar to Fab, indicating that the single chain antibody produced in *C. reinhardtii* is a fully functional antibody. These results clearly demonstrate the ability of the chloroplast to synthesis and accumulate function antibody molecules resulting from the translational activation of an RB47 binding site in an expression cassette by endogenous RB47 protein in the chloroplast.

2) Expression of Bacterial Luciferase Enzyme Having Two Subunits

Figure 9:
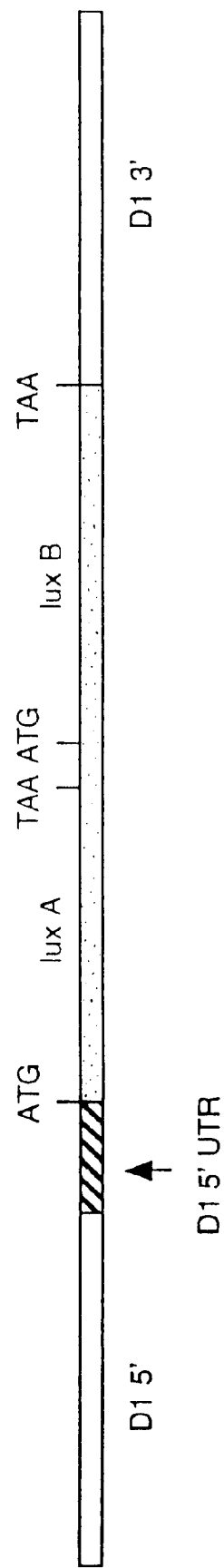
FIG. 9 is a schematic diagram of an expression cassette containing on one transcription unit from 5' to 3', a promoter region derived from the psbA gene for encoding the D1 protein from *C. reinhardtii* further containing a transcription initiation site (TS), the RB47 binding site, a region for insertion of a coding sequence of bacterial luciferase A and B proteins including the translation termination codon TAA. The 3' flanking region containing transcription termination site (TS). Restriction endonuclease sites for facilitating insertion of the independent genetic elements are indicated and further described in Example 4G2).
Figure 10:
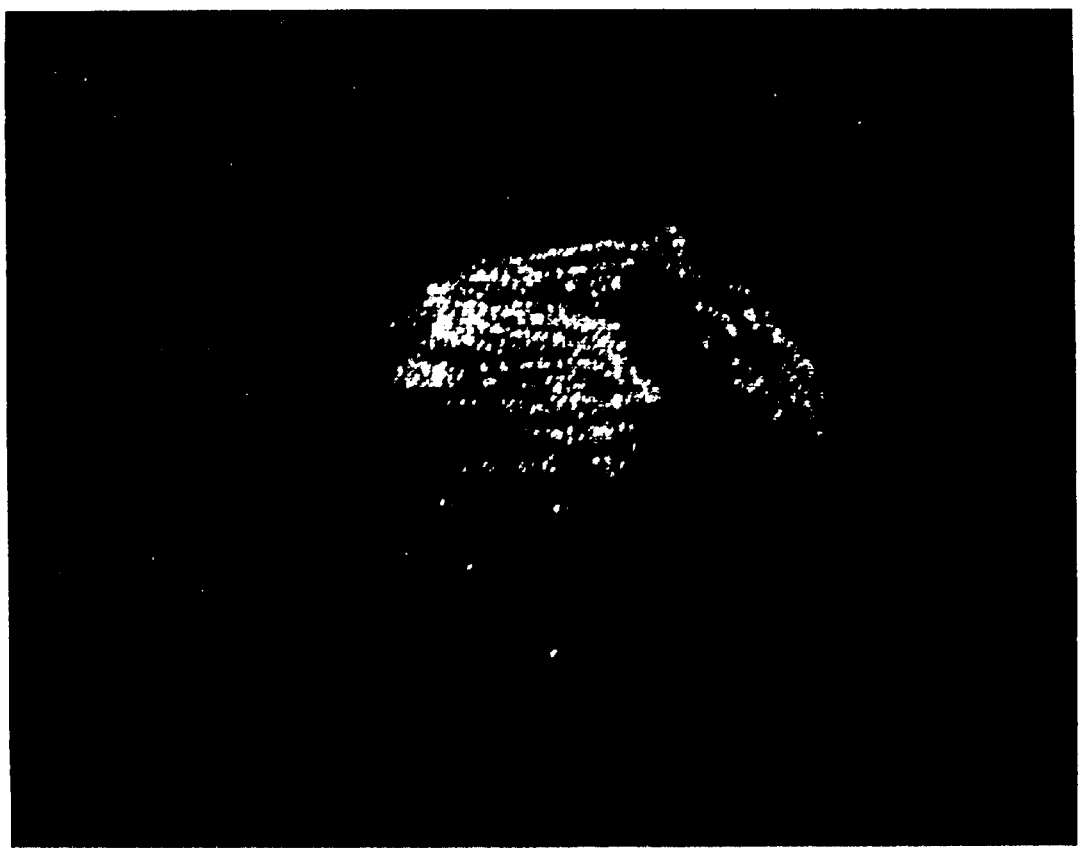
FIG. 10 illustrates the accumulation of expressed bacterial luciferase protein in the chloroplast as further described in Example 4G2).

For the production of molecules that contain more than one subunit, such as dIgA and bacterial luciferase enzyme, several proteins must be produced in stoichiometric quantities within the chloroplast. Chloroplast have an advantage for this type of production over cytoplasmic protein synthesis in that translation of multiple proteins can originate from a single mRNA. For example, a dicistronic mRNA having 5' and 3' NdeI and XbaI restriction sites and containing both the A and B chains of the bacterial luciferase enzyme was inserted downstream of the psbA promoter and 5' UTR of the pD1/Nde construct prepared in Example 4A above. In this construct, the bacterial LuxAB coding region was ligated between the psbA 5' UTR and the psbA 3' end in an *E. coli* plasmid that was then transformed into *Chlamydomonas reinhardtii* cells as described above for expression in the chloroplast. A schematic of the construct is shown in FIG. 9. Single transformant colonies were then isolated. A plate containing a single isolate was grown for 10 days on complete media and a drop of the luciferase substrate n-Decyl Aldehyde was placed on the plate and the luciferase visualized by video-photography in a dark chamber. Both proteins were synthesized from this single mRNA and luciferase activity accumulated within the chloroplast as shown in FIG. 10. Some mRNA within plastids contained as many as 5 separate proteins encoded on a single mRNA.

3) Expression of Dimeric IgA

Figure 11:
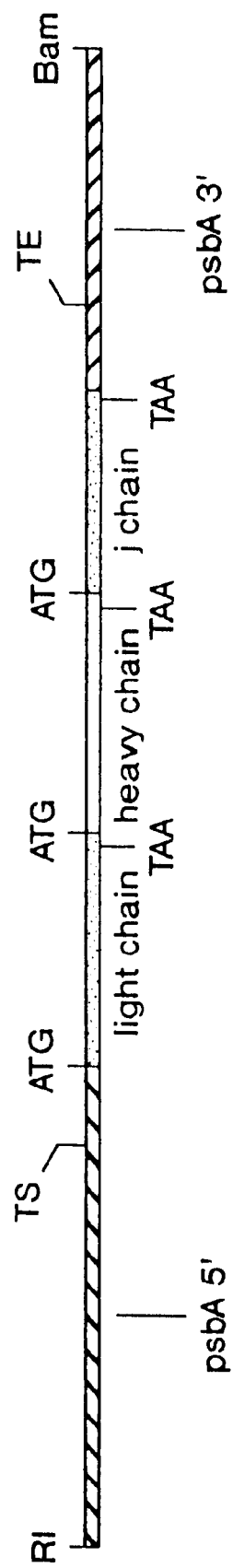
FIG. 11 is a schematic diagram of an expression cassette containing on one transcription unit from 5' to 3', a promoter region derived from the psbA gene for encoding the D1 protein from *C. reinhardtii* further containing a transcription initiation site (TS), the RB47 binding site, a region for insertion of a foreign or heterologous coding region for dimeric IgA (dIgA) and the 3' flanking region containing transcription termination site (TS). Restriction endonuclease sites for facilitating insertion of the independent genetic elements are indicated and further described in Example 4G3).

To generate dimeric IgA, the construct shown in FIG. 11 is engineered so that the psbA promoter and 5' UTR are used to drive the synthesis of the light chain and heavy chains of an antibody, and the J chain normally associated with IgA molecules. The nucleic acid sequences for the dimeric IgA are inserted into the RB47 binding site construct prepared in Example 4A. The construct is then transformed into *C. reinhardtii* cells as previously described for expression of the recombinant dIgA.

Production of these three proteins within the plastid allows for the self assembly of a dimeric IgA (dIgA). Production of this complex is monitored in several ways. First, Southern analysis of transgenic algae is used to identify strains containing the polycistronic chimeric dIgA gene. Strains positive for integration of the dIgA gene are screened by Northern analysis to ensure that the chimeric mRNA is accumulating. Western blot analysis using denaturing gels is used to monitor the accumulation of the individual light, heavy and J chain proteins, and native gels Western blot analysis will be used to monitor the accumulation of the assembled dIgA molecule.

By using a single polycistronic mRNA in the context of RB47 regulated translation, two of the potential pitfalls in the assembly of multimeric dIgA molecule are overcome. First, this construct ensures approximately stoichiometric synthesis of the subunits, as ribosomes reading through the first protein are likely to continue to read through the second and third proteins as well. Second, all of the subunits are synthesized in close physical proximity to each other, which increases the probability of the proteins self assembling into a multimeric molecule. Following the production of a strain producing dIgA molecules, the production of dIgA on an intermediate scale by growing algae in 300 liter fermentors is then performed. Larger production scales are then performed thereafter.

The foregoing specification, including the specific embodiments and examples, is intended to be illustrative of the present invention and is not to be taken as limiting. Numerous other variations and modifications can be effected without departing from the true spirit and scope of the invention.

What is claimed is:

1. A recombinant RB60 protein.

* * * * *

SEQUENCE LISTING

<160> NUMBER OF SEQ ID NOS: 14

<210> SEQ ID NO 1
<211> LENGTH: 15
<212> TYPE: PRT
<213> ORGANISM: Chlamydomonas reinhardtii

<400> SEQUENCE: 1

Gln Tyr Gly Phe Val His Phe Glu Asp Gln Ala Ala Ala Asp Arg
 1               5                  10                  15

<210> SEQ ID NO 2
<211> LENGTH: 14
<212> TYPE: PRT
<213> ORGANISM: Chlamydomonas reinhardtii

<400> SEQUENCE: 2

Gly Phe Gly Phe Ile Asn Phe Lys Asp Ala Glu Ser Ala Ala
 1               5                  10

<210> SEQ ID NO 3
<211> LENGTH: 32

-continued

```
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 3
cagtacggyt tcgtbcaytt cgaggaycag gc                                    32

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 4
ggaattcggy ttcggyttca tyaacttcaa ggaygcbgag                            40

<210> SEQ ID NO 5
<211> LENGTH: 2846
<212> TYPE: DNA
<213> ORGANISM: Chlamydomonas reinhardtii
<220> FEATURE:
<221> NAME/KEY: CDS
<222> LOCATION: (197)..(2065)

<400> SEQUENCE: 5
gaattcgcgg ccgctccgtg gttggtcctc atggtgtctt tttgaagagg acctgagcct      60
ttcacccaaa tatatcaaaa aacccgggca accggccaaa aaaattgcaa aagcctctcg     120
taggcacaaa agacctattc tagccatcaa ctttgtatcc gacgctgccg tttagctgcg     180
cgtcttgaag tcaagc atg gcg act act gag tcc tcg gcc ccg gcg gcc acc    232
               Met Ala Thr Thr Glu Ser Ser Ala Pro Ala Ala Thr
                 1               5                  10 acc cag ccg gcc agc acc ccg ctg gcg aac tcg tcg ctg tac gtc ggt      280
Thr Gln Pro Ala Ser Thr Pro Leu Ala Asn Ser Ser Leu Tyr Val Gly
         15                  20                  25 gac ctg gag aag gat gtc acc gag gcc cag ctg ttc gag ctc ttc tcc      328
Asp Leu Glu Lys Asp Val Thr Glu Ala Gln Leu Phe Glu Leu Phe Ser
     30                  35                  40 tcg gtt ggc cct gtg gcc tcc att cgc gtg tgc cgc gat gcc gtc acg      376
Ser Val Gly Pro Val Ala Ser Ile Arg Val Cys Arg Asp Ala Val Thr
 45                  50                  55                  60 cgc cgc tcg ctg ggc tac gcc tac gtc aac tac aac agc gct ctg gac      424
Arg Arg Ser Leu Gly Tyr Ala Tyr Val Asn Tyr Asn Ser Ala Leu Asp
             65                  70                  75 ccc cag gct gct gac cgc gcc atg gag acc ctg aac tac cat gtc gtg      472
Pro Gln Ala Ala Asp Arg Ala Met Glu Thr Leu Asn Tyr His Val Val
         80                  85                  90 aac ggc aag cct atg cgc atc atg tgg tcg cac cgc gac cct tcg gcc      520
Asn Gly Lys Pro Met Arg Ile Met Trp Ser His Arg Asp Pro Ser Ala
     95                 100                 105 cgc aag tcg ggc gtc ggc aac atc ttc atc aag aac ctg gac aag acc      568
Arg Lys Ser Gly Val Gly Asn Ile Phe Ile Lys Asn Leu Asp Lys Thr
110                 115                 120 atc gac gcc aag gcc ctg cac gac acc ttc tcg gcc ttc ggc aag att      616
Ile Asp Ala Lys Ala Leu His Asp Thr Phe Ser Ala Phe Gly Lys Ile
125                 130                 135                 140 ctg tcc tgc aag gtt gcc act gac gcc aac ggc gtg tcg aag ggc tac      664
Leu Ser Cys Lys Val Ala Thr Asp Ala Asn Gly Val Ser Lys Gly Tyr
                145                 150                 155
```

```
ggc ttc gtg cac ttc gag gac cag gcc gct gcc gat cgc gcc att cag      712
Gly Phe Val His Phe Glu Asp Gln Ala Ala Asp Arg Ala Ile Gln
            160                 165                 170 acc gtc aac cag aag aag att gag ggc aag atc gtg tac gtg gcc ccc      760
Thr Val Asn Gln Lys Lys Ile Glu Gly Lys Ile Val Tyr Val Ala Pro
        175                 180                 185 ttc cag aag cgc gct gac cgc ccc agg gca agg acg ttg tac acc aac      808
Phe Gln Lys Arg Ala Asp Arg Pro Arg Ala Arg Thr Leu Tyr Thr Asn
    190                 195                 200 gtg ttc gtc aag aac ttg ccg gcc gac atc ggc gac gag ctg ggc          856
Val Phe Val Lys Asn Leu Pro Ala Asp Ile Gly Asp Asp Glu Leu Gly
205                 210                 215                 220 aag atg gcc acc gag cac ggc gag atc acc agc gcg gtg gtc atg aag      904
Lys Met Ala Thr Glu His Gly Glu Ile Thr Ser Ala Val Val Met Lys
            225                 230                 235 gac gac aag ggc ggc agc aag ggc ttc ggc ttc atc aac ttc aag gac      952
Asp Asp Lys Gly Gly Ser Lys Gly Phe Gly Phe Ile Asn Phe Lys Asp
        240                 245                 250 gcc gag tcg gcg gcc aag tgc gtg gag tac ctg aac gag cgc gag atg     1000
Ala Glu Ser Ala Ala Lys Cys Val Glu Tyr Leu Asn Glu Arg Glu Met
    255                 260                 265 agc ggc aag acc ctg tac gcc ggc cgc gcc cag aag aag acc gag cgc     1048
Ser Gly Lys Thr Leu Tyr Ala Gly Arg Ala Gln Lys Lys Thr Glu Arg
270                 275                 280 gag gcg atg ctg cgc cag aag gcc gag gag agc aag cag gag cgt tac     1096
Glu Ala Met Leu Arg Gln Lys Ala Glu Glu Ser Lys Gln Glu Arg Tyr
285                 290                 295                 300 ctg aag tac cag agc atg aac ctg tac gtc aag aac ctg tcc gac gag     1144
Leu Lys Tyr Gln Ser Met Asn Leu Tyr Val Lys Asn Leu Ser Asp Glu
            305                 310                 315 gag gtc gac gac gac gcc ctg cgt gag ctg ttc gcc aac tct ggc acc     1192
Glu Val Asp Asp Asp Ala Leu Arg Glu Leu Phe Ala Asn Ser Gly Thr
        320                 325                 330 atc acc tcg tgc aag gtc atg aag gac ggc agc ggc aag tcc aag ggc     1240
Ile Thr Ser Cys Lys Val Met Lys Asp Gly Ser Gly Lys Ser Lys Gly
    335                 340                 345 ttc ggc ttc gtg tgc ttc acc agc cac gac gag gcc acc cgg ccg ccc     1288
Phe Gly Phe Val Cys Phe Thr Ser His Asp Glu Ala Thr Arg Pro Pro
350                 355                 360 gtg acc gag atg aac ggc aag atg gtc aag ggc aag ccc ctg tac gtg     1336
Val Thr Glu Met Asn Gly Lys Met Val Lys Gly Lys Pro Leu Tyr Val
365                 370                 375                 380 gcc ctg gcg cag cgc aag gac gtg cgc cgt gcc acc cag ctg gag gcc     1384
Ala Leu Ala Gln Arg Lys Asp Val Arg Arg Ala Thr Gln Leu Glu Ala
            385                 390                 395 aac atg cag gcg cgc atg ggc atg ggc gcc atg agc cgc ccg ccg aac     1432
Asn Met Gln Ala Arg Met Gly Met Gly Ala Met Ser Arg Pro Pro Asn
        400                 405                 410 ccg atg gcc ggc atg agc ccc tac ccc ggc gcc atg ccg ttc ttc gct     1480
Pro Met Ala Gly Met Ser Pro Tyr Pro Gly Ala Met Pro Phe Phe Ala
    415                 420                 425 ccc ggc ccc ggc ggc atg gct gct ggc ccg cgc gct ccg ggc atg atg     1528
Pro Gly Pro Gly Gly Met Ala Ala Gly Pro Arg Ala Pro Gly Met Met
430                 435                 440 tac ccg ccc atg atg ccg ccg cgc ggc atg cct ggc ccc ggc cgc ggc     1576
Tyr Pro Pro Met Met Pro Pro Arg Gly Met Pro Gly Pro Gly Arg Gly
445                 450                 455                 460 ccc cgc ggc ccc atg atg ccg ccc cag atg atg ggt ggc ccc atg atg     1624
Pro Arg Gly Pro Met Met Pro Pro Gln Met Met Gly Gly Pro Met Met
```

```
              465                 470                 475
ggc ccg ccc atg ggc ccc ggg cgc ggc cgt ggc ggc cgc ggc ccc tcc    1672
Gly Pro Pro Met Gly Pro Gly Arg Gly Arg Gly Gly Arg Gly Pro Ser
            480                 485                 490 ggc cgc ggc cag ggc cgc ggc aac aac gcc cct gcc cag cag ccc aag    1720
Gly Arg Gly Gln Gly Arg Gly Asn Asn Ala Pro Ala Gln Gln Pro Lys
        495                 500                 505 ccc gcc gct gag ccg gcc gcc gcg ccc gcc gcc gcc ccc gct gcc        1768
Pro Ala Ala Glu Pro Ala Ala Ala Pro Ala Ala Ala Pro Ala Ala
    510                 515                 520 gcg gcg cct gcc gcc gcg gcg gag ccg gag gcc ccc gcc gcc cag cag    1816
Ala Ala Pro Ala Ala Ala Ala Glu Pro Glu Ala Pro Ala Ala Gln Gln
525                 530                 535                 540 ccg ctg acc gcc tcc gcg ctg gcc gcc gcc gcg ccg gag cag cag aag    1864
Pro Leu Thr Ala Ser Ala Leu Ala Ala Ala Ala Pro Glu Gln Gln Lys
            545                 550                 555 atg atg atc ggc gag cgc ctg tac ccg cag gtg gcg gag ctg cag ccc    1912
Met Met Ile Gly Glu Arg Leu Tyr Pro Gln Val Ala Glu Leu Gln Pro
        560                 565                 570 gac ctg gct ggc aag atc acc ggc atg ctg ctg gag atg gac aac gcc    1960
Asp Leu Ala Gly Lys Ile Thr Gly Met Leu Leu Glu Met Asp Asn Ala
    575                 580                 585 gag ctt ctg atg ctt ctg gag tcg cac gag gcg ctg gtg tcc aag gtg    2008
Glu Leu Leu Met Leu Leu Glu Ser His Glu Ala Leu Val Ser Lys Val
        590                 595                 600 gac gag gcc atc gct gtg ctc aag cag cac aac gtg att gcc gag gag    2056
Asp Glu Ala Ile Ala Val Leu Lys Gln His Asn Val Ile Ala Glu Glu
605                 610                 615                 620 aac aag gct taaagcgcct gcacgcttgt gcgggctggt ggcgccggcg            2105
Asn Lys Ala cgcgccggcg ctgcttgggc cgccggcagc atgggcgcgg cggacgcggt gtgggagcag    2165
tgcttgctgc ttctggccgc cgtgaagccg cgccgaactg gggcggacgg caggctggcg    2225
ttgacgccgg cgcgccacaa cacaaagttg gtggcgtgaa agtctctggg cgtgctccgg    2285
acggttgtaa ggttttaaga actggctttt ggccgggttg ccgcccaaag gcggaacggc    2345
ggtcttttca ggccaatcac atccggctgg aaaaattctt accaaagcca accccctgcac    2405 ccaaaaattt cgggttccga agaacactc ccctttttc cggcaacgcg ttctttcaag     2465
gccaatcact ttccgggttg gaagaaaatg ttacccggaa aaggcgggaa gcccctgca     2525 cccggacaag ttattcgggg tttcgccggg aatgagcaag cgttcgggct gttggccgta    2585
tcgcgaacgc tgtcggggtg tcaggcgcca gaaggaagga tgacgttttg gtgaaggggt    2645
gcaaactgag cacacgagtt ttggcaatag acgtggagaa agtccagtgc ggggtgaggc    2705
ggatagcgga atcaagcgtg gcgggtccct ggcgagacga gacgcttctg ttgtttttgct  2765 gagcccttg atggcacaat cgcactgttt tgagcaggcg actgtaaagt gcccgacgct    2825
aaaaaagcgg ccgcgaattc c                                            2846
```

<210> SEQ ID NO 6
<211> LENGTH: 15
<212> TYPE: PRT
<213> ORGANISM: Chlamydomonas reinhardtii

<400> SEQUENCE: 6

Trp Phe Val Asp Gly Glu Leu Ala Ser Asp Tyr Asn Gly Pro Arg
 1               5                  10                  15

```
<210> SEQ ID NO 7
<211> LENGTH: 22
<212> TYPE: PRT
<213> ORGANISM: Chlamydomonas reinhardtii

<400> SEQUENCE: 7

Gln Leu Ile Leu Trp Thr Thr Ala Asp Asp Leu Lys Ala Asp Ala Glu
 1               5                  10                  15

Ile Met Thr Val Phe Arg
            20

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 8
cgcggatccg aygcbgagat yatgac                                           26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 9
cgcgaattcg tcatratctc vgcrtc                                           26

<210> SEQ ID NO 10
<211> LENGTH: 2413
<212> TYPE: DNA
<213> ORGANISM: Chlamydomonas reinhardtii
<220> FEATURE:
<221> NAME/KEY: CDS
<222> LOCATION: (16)..(1614)

<400> SEQUENCE: 10
gagtacgttt acgcc atg aac cgt tgg aac ctt ctt gcc ctt acc ctg ggg        51
                 Met Asn Arg Trp Asn Leu Leu Ala Leu Thr Leu Gly
                  1               5                  10 ctg ctg ctg gtg gca gcg ccc ttc acc aag cac cag ttt gct cat gct        99
Leu Leu Leu Val Ala Ala Pro Phe Thr Lys His Gln Phe Ala His Ala
        15                  20                  25 tcc gat gag tat gag gac gac gag gag gac gat gcc ccc gcc gcc cct       147
Ser Asp Glu Tyr Glu Asp Asp Glu Glu Asp Asp Ala Pro Ala Ala Pro
    30                  35                  40 aag gac gac gac gtc gac gtt act gtg gtg acc gtc aag aac tgg gat       195
Lys Asp Asp Asp Val Asp Val Thr Val Val Thr Val Lys Asn Trp Asp
45                  50                  55                  60 gag acc gtc aag aag tcc aag ttc gcg ctt gtg gag ttc tac gct cct       243
Glu Thr Val Lys Lys Ser Lys Phe Ala Leu Val Glu Phe Tyr Ala Pro
                65                  70                  75 tgg tgc ggc cac tgc aag acc ctc aag cct gag tac gct aag gct gcc       291
Trp Cys Gly His Cys Lys Thr Leu Lys Pro Glu Tyr Ala Lys Ala Ala
            80                  85                  90 acc gcc ctg aag gct gct gct ccc gat gcc ctt atc gcc aag gtc gac       339
Thr Ala Leu Lys Ala Ala Ala Pro Asp Ala Leu Ile Ala Lys Val Asp
        95                 100                 105 gcc acc cag gag gag tcc ctg gcc cag aag ttc ggc gtg cag ggc tac       387
```

-continued

```
Ala Thr Gln Glu Glu Ser Leu Ala Gln Lys Phe Gly Val Gln Gly Tyr
        110                 115                 120 ccc acc ctc aag tgg ttc gtt gat ggc gag ctg gct tct gac tac aac      435
Pro Thr Leu Lys Trp Phe Val Asp Gly Glu Leu Ala Ser Asp Tyr Asn
125                 130                 135                 140 ggc ccc cgc gac gct gat ggc att gtt ggc tgg gtg aag aag aag act      483
Gly Pro Arg Asp Ala Asp Gly Ile Val Gly Trp Val Lys Lys Lys Thr
                145                 150                 155 ggc ccc ccc gcc gtg acc gtt gag gac gcc gac aag ctg aag tcc ctg      531
Gly Pro Pro Ala Val Thr Val Glu Asp Ala Asp Lys Leu Lys Ser Leu
            160                 165                 170 gag gcg gac gct gag gtc gtt gtc gtc ggc tac ttc aag gcc ctg gag      579
Glu Ala Asp Ala Glu Val Val Val Val Gly Tyr Phe Lys Ala Leu Glu
        175                 180                 185 ggc gag atc tac gac acc ttc aag tcc tac gcc gcc aag acc gag gac      627
Gly Glu Ile Tyr Asp Thr Phe Lys Ser Tyr Ala Ala Lys Thr Glu Asp
    190                 195                 200 gtg gtg ttc gtg cag acc acc agc gcc gac gtc gcc aag gcc gcc ggc      675
Val Val Phe Val Gln Thr Thr Ser Ala Asp Val Ala Lys Ala Ala Gly
205                 210                 215                 220 ctg gac gcc gtg gac acc gtg tcc gtg gtc aag aac ttc gcc ggt gag      723
Leu Asp Ala Val Asp Thr Val Ser Val Val Lys Asn Phe Ala Gly Glu
                225                 230                 235 gac cgc gcc acc gcc gtc ctg gcc acg gac atc gac act gac tcc ctg      771
Asp Arg Ala Thr Ala Val Leu Ala Thr Asp Ile Asp Thr Asp Ser Leu
            240                 245                 250 acc gcg ttc gtc aag tcg gag aag atg ccc ccc acc att gag ttc aac      819
Thr Ala Phe Val Lys Ser Glu Lys Met Pro Pro Thr Ile Glu Phe Asn
        255                 260                 265 cag aag aac tct gac aag atc ttc aac agc ggc atc aac aag cag ctg      867
Gln Lys Asn Ser Asp Lys Ile Phe Asn Ser Gly Ile Asn Lys Gln Leu
    270                 275                 280 att ctg tgg acc acc gcc gac gac ctg aag gcc gac gcc gag atc atg      915
Ile Leu Trp Thr Thr Ala Asp Asp Leu Lys Ala Asp Ala Glu Ile Met
285                 290                 295                 300 act gtg ttc cgc gag gcc agc aag aag ttc aag ggc cag ctg gtg ttc      963
Thr Val Phe Arg Glu Ala Ser Lys Lys Phe Lys Gly Gln Leu Val Phe
                305                 310                 315 gtg acc gtc aac aac gag ggc gac ggc gcc gac ccc gtc acc aac ttc     1011
Val Thr Val Asn Asn Glu Gly Asp Gly Ala Asp Pro Val Thr Asn Phe
            320                 325                 330 ttc ggc ctc aag ggc gcc acc tcg cct gtg ctg ctg ggc ttc ttc atg     1059
Phe Gly Leu Lys Gly Ala Thr Ser Pro Val Leu Leu Gly Phe Phe Met
        335                 340                 345 gag aag aac aag aag ttc cgc atg gag ggc gag ttc acg gct gac aac     1107
Glu Lys Asn Lys Lys Phe Arg Met Glu Gly Glu Phe Thr Ala Asp Asn
    350                 355                 360 gtg gct aag ttc gcc gag agc gtg gtg gac ggc acc gcg cag gcc gtg     1155
Val Ala Lys Phe Ala Glu Ser Val Val Asp Gly Thr Ala Gln Ala Val
365                 370                 375                 380 ctc aag tcg gag gcc atc ccc gag gac ccc tat gag gat ggc gtc tac     1203
Leu Lys Ser Glu Ala Ile Pro Glu Asp Pro Tyr Glu Asp Gly Val Tyr
                385                 390                 395 aag att gtg ggc aag acc gtg gag tct gtg gtt ctg gac gag acc aag     1251
Lys Ile Val Gly Lys Thr Val Glu Ser Val Val Leu Asp Glu Thr Lys
            400                 405                 410 gac gtg ctg ctg gag gtg tac gcc ccc tgg tgc ggc cac tgc aag aag     1299
Asp Val Leu Leu Glu Val Tyr Ala Pro Trp Cys Gly His Cys Lys Lys
        415                 420                 425
```

```
ctg gag ccc atc tac aag aag ctg gcc aag cgc ttt aag aag gtg gat      1347
Leu Glu Pro Ile Tyr Lys Lys Leu Ala Lys Arg Phe Lys Lys Val Asp
        430                 435                 440 tcc gtc atc atc gcc aag atg gat ggc act gag aac gag cac ccc gag      1395
Ser Val Ile Ile Ala Lys Met Asp Gly Thr Glu Asn Glu His Pro Glu
445                 450                 455                 460 atc gag gtc aag ggc ttc cct acc atc ctg ttc tat ccc gcc ggc agc      1443
Ile Glu Val Lys Gly Phe Pro Thr Ile Leu Phe Tyr Pro Ala Gly Ser
                465                 470                 475 gac cgc acc ccc atc gtg ttc gag ggc ggc gac cgc tcg ctc aag tcc      1491
Asp Arg Thr Pro Ile Val Phe Glu Gly Gly Asp Arg Ser Leu Lys Ser
            480                 485                 490 ctg acc aag ttc atc aag acc aac gcc aag atc ccg tac gag ctg ccc      1539
Leu Thr Lys Phe Ile Lys Thr Asn Ala Lys Ile Pro Tyr Glu Leu Pro
        495                 500                 505 aag aag ggc tcc gac ggc gac gag ggc acc tcg gac gac aag gac aag      1587
Lys Lys Gly Ser Asp Gly Asp Glu Gly Thr Ser Asp Asp Lys Asp Lys
    510                 515                 520 ccc gcg tcc gac aag gac gag ctg taa gcggctatct gaactacccc            1634
Pro Ala Ser Asp Lys Asp Glu Leu
525                 530 aggtttggag cgtctgcttg cgcgcttgcg cttgcacact gtgcatggat gggagttaag    1694
gaggagacgg agcacggagg ctgcgctcgg ttggtggctt ggagcaccgg cagcgcgtga    1754
tccgtcctgg cagcagcaac ggcggagcgg gcgcatattg gcgcgagctg gcgagcggct    1814
gttgctggag aggatatgct gccgggcggg aggaagggc agggggcagag atgagagcgt    1874 tacgggctgg catgcgggcg cccgtgcctc tccctgcggt gcagtccttg ctaggagacg    1934
cacggttttg ccaaagaggg acgctgtcca cagccctgcg actggaagtt ttttaggccc    1994
tgcggtggta gtggtgttgg tacggttgtg tgcataagat gaacaacgtt tctctcaaga    2054
cgagactact agtatgctga cggtgtgtgt atgtggtgga tggattgtgc cccgaccatg    2114
aagagtgctg tgttgcctcg gcgcttctgt cgccctggat gtgcgtggtt ccgaacgctg    2174
gagtcatctg ttgaggagcg agggtgttgt cgggtccgcc cggcacggcc gcgtgatgtc    2234
cggatgggga ttgcgagcga gggcaaccgc agcgcagata gcgccgcagc ggatcgagct    2294
agcgcaggat gatgagagcc gggccttcgc ggcgtgggat cagggaggag ccaaggcgga    2354
gtgcatgcga ggaaaacagt gtgcggcaaa gaacgggctg caagaacgcc ttgcgcaaa     2413
```

<210> SEQ ID NO 11
<211> LENGTH: 4
<212> TYPE: PRT
<213> ORGANISM: Chlamydomonas reinhardtii

<400> SEQUENCE: 11

Cys Gly His Cys
 1

<210> SEQ ID NO 12
<211> LENGTH: 4
<212> TYPE: PRT
<213> ORGANISM: Chlamydomonas reinhardtii

<400> SEQUENCE: 12

Lys Asp Glu Leu
 1

<210> SEQ ID NO 13
<211> LENGTH: 1424

```
<212> TYPE: DNA
<213> ORGANISM: Chlamydomonas reinhardtii
<220> FEATURE:
<221> NAME/KEY: CDS
<222> LOCATION: (252)..(1310)
<221> NAME/KEY: misc_feature
<222> LOCATION: (279)
<223> OTHER INFORMATION: Codon also can encode Ser
<221> NAME/KEY: misc_feature
<222> LOCATION: (282)
<223> OTHER INFORMATION: Codon also can encode Glu
<221> NAME/KEY: misc_feature
<222> LOCATION: (294)
<223> OTHER INFORMATION: Codon also can encode Gly
<221> NAME/KEY: misc_feature
<222> LOCATION: (306)
<223> OTHER INFORMATION: Codon also can encode Asn
<221> NAME/KEY: misc_feature
<222> LOCATION: (357)
<223> OTHER INFORMATION: Codon also can encode Leu
<221> NAME/KEY: misc_feature
<222> LOCATION: (369)
<223> OTHER INFORMATION: Codon also can encode Thr
<221> NAME/KEY: misc_feature
<222> LOCATION: (486)
<223> OTHER INFORMATION: Codon also can encode Ser
<221> NAME/KEY: misc_feature
<222> LOCATION: (495)
<223> OTHER INFORMATION: Codon also can encode Ile
<221> NAME/KEY: misc_feature
<222> LOCATION: (510)
<223> OTHER INFORMATION: Codon also can encode Ala
<221> NAME/KEY: misc_feature
<222> LOCATION: (555)
<223> OTHER INFORMATION: Codon also can encode Val
<221> NAME/KEY: misc_feature
<222> LOCATION: (588)
<223> OTHER INFORMATION: Codon also can encode Glu
<221> NAME/KEY: misc_feature
<222> LOCATION: (600)
<223> OTHER INFORMATION: Codon also can encode Leu
<221> NAME/KEY: misc_feature
<222> LOCATION: (621)
<223> OTHER INFORMATION: Codon also can encode Ala
<221> NAME/KEY: misc_feature
<222> LOCATION: (714)
<223> OTHER INFORMATION: Codon also can encode Thr
<221> NAME/KEY: misc_feature
<222> LOCATION: (729)
<223> OTHER INFORMATION: Codon also can encode Ile
<221> NAME/KEY: misc_feature
<222> LOCATION: (1092)
<223> OTHER INFORMATION: Codon also can encode Val
<221> NAME/KEY: misc_feature
<222> LOCATION: (1191)
<223> OTHER INFORMATION: Codon also can encode Ile
<221> NAME/KEY: misc_feature
<222> LOCATION: (1284)
<223> OTHER INFORMATION: Codon also can encode Ala
<221> NAME/KEY: misc_feature
<222> LOCATION: (1287)
<223> OTHER INFORMATION: Codon also can encode Ile
<221> NAME/KEY: misc_feature
<222> LOCATION: (1290)
<223> OTHER INFORMATION: Codon also can encode Glu
<221> NAME/KEY: misc_feature
<222> LOCATION: (1293)
<223> OTHER INFORMATION: Codon also can encode Ala
<221> NAME/KEY: misc_feature
<222> LOCATION: (1296)
<223> OTHER INFORMATION: Codon also can encode Pro
<221> NAME/KEY: misc_feature
<222> LOCATION: (1302)
<223> OTHER INFORMATION: Codon also can encode Thr
<221> NAME/KEY: misc_feature
<222> LOCATION: (1308)
<223> OTHER INFORMATION: Codon also can encode Gly

<400> SEQUENCE: 13
```

-continued

```
cgtcctattt taatactccg aaggaggcag ttggcaggca actgccactg acgtcccgta       60
agggtaaggg gacgtccact ggcgtcccgt aaggggaagg ggacgtaggt acataaatgt      120
gctaggtaac taacgtttga tttttgtgg tataatatat gtaccatgct tttaatagaa      180
gcttgaattt ataaattaaa atattttac aatattttac ggagaaatta aactttaaa       240 aaaattaaca t atg aca gca att tta gaa cgt cgt gaa aat tct agc cta     290
            Met Thr Ala Ile Leu Glu Arg Arg Glu Asn Ser Ser Leu
              1               5                  10 tgg gct cgt ttt tgt gag tgg atc act tca act gaa aac cgt tta tac     338
Trp Ala Arg Phe Cys Glu Trp Ile Thr Ser Thr Glu Asn Arg Leu Tyr
 15                  20                  25 atc ggt tgg ttc ggt gta atc atg atc cca tgt ctt ctt act gca aca     386
Ile Gly Trp Phe Gly Val Ile Met Ile Pro Cys Leu Leu Thr Ala Thr
 30                  35                  40                  45 tca gta ttc atc atc gct ttc atc gct gct ccg cca gta gac atc gat     434
Ser Val Phe Ile Ile Ala Phe Ile Ala Ala Pro Pro Val Asp Ile Asp
                 50                  55                  60 ggt atc cgt gaa cca gtt tca ggt tct ctt ctt tac ggt aac aac atc     482
Gly Ile Arg Glu Pro Val Ser Gly Ser Leu Leu Tyr Gly Asn Asn Ile
             65                  70                  75 att aca ggt gct gta atc cca act tct aac gca atc ggt ctt cac ttc     530
Ile Thr Gly Ala Val Ile Pro Thr Ser Asn Ala Ile Gly Leu His Phe
         80                  85                  90 tac cca att tgg gaa gct gct tct cta gac gag tgg tta tac aac ggt     578
Tyr Pro Ile Trp Glu Ala Ala Ser Leu Asp Glu Trp Leu Tyr Asn Gly
     95                 100                 105 ggt cct tac caa ctt atc gtt tgt cac ttc ctt cta ggt gta tac tgc     626
Gly Pro Tyr Gln Leu Ile Val Cys His Phe Leu Leu Gly Val Tyr Cys
110                 115                 120                 125 tac atg ggt cgt gag tgg gaa tta tct ttc cgt tta ggt atg cgt cca     674
Tyr Met Gly Arg Glu Trp Glu Leu Ser Phe Arg Leu Gly Met Arg Pro
                130                 135                 140 tgg atc gct gta gct tac tca gct cca gta gct gca gct tca gct gta     722
Trp Ile Ala Val Ala Tyr Ser Ala Pro Val Ala Ala Ala Ser Ala Val
            145                 150                 155 ttc tta gtt tac cct atc ggc caa ggt tca ttc tct gac ggt atg cct     770
Phe Leu Val Tyr Pro Ile Gly Gln Gly Ser Phe Ser Asp Gly Met Pro
        160                 165                 170 tta ggt atc tct ggt act ttc aac ttc atg atc gta ttc caa gca gaa     818
Leu Gly Ile Ser Gly Thr Phe Asn Phe Met Ile Val Phe Gln Ala Glu
    175                 180                 185 cac aac atc ctt atg cac cca ttc cac atg tta ggt gtt gct ggt gta     866
His Asn Ile Leu Met His Pro Phe His Met Leu Gly Val Ala Gly Val
190                 195                 200                 205 ttc ggt ggt tca tta ttc tca gct atg cac ggt tct tta gtt act tca     914
Phe Gly Gly Ser Leu Phe Ser Ala Met His Gly Ser Leu Val Thr Ser
                210                 215                 220 tct tta atc cgt gaa aca act gaa aac gaa tca gct aac gaa ggt tac     962
Ser Leu Ile Arg Glu Thr Thr Glu Asn Glu Ser Ala Asn Glu Gly Tyr
            225                 230                 235 cgt ttc ggt caa gaa gaa gaa act tac aac att gta gct gct cat ggt    1010
Arg Phe Gly Gln Glu Glu Glu Thr Tyr Asn Ile Val Ala Ala His Gly
        240                 245                 250 tac ttt ggt cgt cta atc ttc caa tac gct tct ttc aac aac tct cgt    1058
Tyr Phe Gly Arg Leu Ile Phe Gln Tyr Ala Ser Phe Asn Asn Ser Arg
    255                 260                 265 tca tta cac ttc ttc tta gct gct tgg ccg gta atc ggt att tgg ttc    1106
Ser Leu His Phe Phe Leu Ala Ala Trp Pro Val Ile Gly Ile Trp Phe
```

```
                270               275               280               285
act gct tta ggt tta tca act atg gca ttc aac tta aac ggt ttc aac        1154
Thr Ala Leu Gly Leu Ser Thr Met Ala Phe Asn Leu Asn Gly Phe Asn
                290               295               300 ttc aac caa tca gta gta gac tca caa ggt cgt gta cta aac act tgg        1202
Phe Asn Gln Ser Val Val Asp Ser Gln Gly Arg Val Leu Asn Thr Trp
            305               310               315 gca gac atc atc aac cgt gct aac tta ggt atg gaa gta atg cac gag        1250
Ala Asp Ile Ile Asn Arg Ala Asn Leu Gly Met Glu Val Met His Glu
        320               325               330 cgt aac gct cac aac ttc cct cta gac tta gct tca act aac tct agc        1298
Arg Asn Ala His Asn Phe Pro Leu Asp Leu Ala Ser Thr Asn Ser Ser
    335               340               345 tca aac aac taa ttttttttta aactaaaata aatctggtta accataccta            1350
Ser Asn Asn
350 gtttatttta gtttatacac acttttcata tatatatact taatagctac cataggcagt     1410 tggcaggacg tccc                                                        1424

<210> SEQ ID NO 14
<211> LENGTH: 1278
<212> TYPE: DNA
<213> ORGANISM: Chlamydomonas reinhardtii
<220> FEATURE:
<221> NAME/KEY: CDS
<222> LOCATION: (1)..(1272)

<400> SEQUENCE: 14 atg ggc cat cat cat cat cat cat cat cat cac agc agc ggc cat            48
Met Gly His His His His His His His His His Ser Ser Gly His
1               5                   10                  15 atc gaa ggt cgt cat atg gcg act act gag tcc tcg gcc ccg gcg gcc        96
Ile Glu Gly Arg His Met Ala Thr Thr Glu Ser Ser Ala Pro Ala Ala
            20                  25                  30 acc acc cag ccg gcc agc acc ccg ctg gcg aac tcg tcg ctg tac gtc       144
Thr Thr Gln Pro Ala Ser Thr Pro Leu Ala Asn Ser Ser Leu Tyr Val
        35                  40                  45 ggt gac ctg gag aag gat gtc acc gag gcc cag ctg ttc gag ctc ttc       192
Gly Asp Leu Glu Lys Asp Val Thr Glu Ala Gln Leu Phe Glu Leu Phe
    50                  55                  60 tcc tcg gtt ggc cct gtg gcc tcc att cgc gtg tgc cgc gat gcc gtc       240
Ser Ser Val Gly Pro Val Ala Ser Ile Arg Val Cys Arg Asp Ala Val
65                  70                  75                  80 acg cgc cgc tcg ctg ggc tac gcc tac gtc aac tac aac agc gct ctg       288
Thr Arg Arg Ser Leu Gly Tyr Ala Tyr Val Asn Tyr Asn Ser Ala Leu
                85                  90                  95 gac ccc cag gct gct gac cgc gcc atg gag acc ctg aac tac cat gtc       336
Asp Pro Gln Ala Ala Asp Arg Ala Met Glu Thr Leu Asn Tyr His Val
            100                 105                 110 gtg aac ggc aag cct atg cgc atc atg tgg tcg cac cgc gac cct tcg       384
Val Asn Gly Lys Pro Met Arg Ile Met Trp Ser His Arg Asp Pro Ser
        115                 120                 125 gcc cgc aag tcg ggc gtc ggc aac atc ttc atc aag aac ctg gac aag       432
Ala Arg Lys Ser Gly Val Gly Asn Ile Phe Ile Lys Asn Leu Asp Lys
    130                 135                 140 acc atc gac gcc aag gcc ctg cac gac acc ttc tcg gcc ttc ggc aag       480
Thr Ile Asp Ala Lys Ala Leu His Asp Thr Phe Ser Ala Phe Gly Lys
145                 150                 155                 160 att ctg tcc tgc aag gtt gcc act gac gcc aac ggc gtg tcg aag ggc       528
Ile Leu Ser Cys Lys Val Ala Thr Asp Ala Asn Gly Val Ser Lys Gly
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 165 |     |     |     |     | 170 |     |     |     |     | 175 |     |      |
| tac | ggc | ttc | gtg | cac | ttc | gag | gac | cag | gcc | gct | gcc | gat | cgc | gcc | att | 576  |
| Tyr | Gly | Phe | Val | His | Phe | Glu | Asp | Gln | Ala | Ala | Ala | Asp | Arg | Ala | Ile |      |
|     |     |     | 180 |     |     |     |     | 185 |     |     |     |     | 190 |     |     |      |
| cag | acc | gtc | aac | cag | aag | aag | att | gag | ggc | aag | atc | gtg | tac | gtg | gcc | 624  |
| Gln | Thr | Val | Asn | Gln | Lys | Lys | Ile | Glu | Gly | Lys | Ile | Val | Tyr | Val | Ala |      |
|     |     | 195 |     |     |     |     | 200 |     |     |     |     | 205 |     |     |     |      |
| ccc | ttc | cag | aag | cgc | gct | gac | cgc | ccc | agg | gca | agg | acg | ttg | tac | acc | 672  |
| Pro | Phe | Gln | Lys | Arg | Ala | Asp | Arg | Pro | Arg | Ala | Arg | Thr | Leu | Tyr | Thr |      |
|     | 210 |     |     |     |     | 215 |     |     |     |     | 220 |     |     |     |     |      |
| aac | gtg | ttc | gtc | aag | aac | ttg | ccg | gcc | gac | atc | ggc | gac | gac | gag | ctg | 720  |
| Asn | Val | Phe | Val | Lys | Asn | Leu | Pro | Ala | Asp | Ile | Gly | Asp | Asp | Glu | Leu |      |
| 225 |     |     |     |     | 230 |     |     |     |     | 235 |     |     |     |     | 240 |      |
| ggc | aag | atg | gcc | acc | gag | cac | ggc | gag | atc | acc | agc | gcg | gtg | gtc | atg | 768  |
| Gly | Lys | Met | Ala | Thr | Glu | His | Gly | Glu | Ile | Thr | Ser | Ala | Val | Val | Met |      |
|     |     |     |     | 245 |     |     |     |     | 250 |     |     |     |     | 255 |     |      |
| aag | gac | gac | aag | ggc | ggc | agc | aag | ggc | ttc | ggc | ttc | atc | aac | ttc | aag | 816  |
| Lys | Asp | Asp | Lys | Gly | Gly | Ser | Lys | Gly | Phe | Gly | Phe | Ile | Asn | Phe | Lys |      |
|     |     |     | 260 |     |     |     |     | 265 |     |     |     |     | 270 |     |     |      |
| gac | gcc | gag | tcg | gcg | gcc | aag | tgc | gtg | gag | tac | ctg | aac | gag | cgc | gag | 864  |
| Asp | Ala | Glu | Ser | Ala | Ala | Lys | Cys | Val | Glu | Tyr | Leu | Asn | Glu | Arg | Glu |      |
|     |     | 275 |     |     |     |     | 280 |     |     |     |     | 285 |     |     |     |      |
| atg | agc | ggc | aag | acc | ctg | tac | gcc | ggc | cgc | gcc | cag | aag | aag | acc | gag | 912  |
| Met | Ser | Gly | Lys | Thr | Leu | Tyr | Ala | Gly | Arg | Ala | Gln | Lys | Lys | Thr | Glu |      |
|     | 290 |     |     |     |     | 295 |     |     |     |     | 300 |     |     |     |     |      |
| cgc | gag | gcg | atg | ctg | cgc | cag | aag | gcc | gag | gag | agc | aag | cag | gag | cgt | 960  |
| Arg | Glu | Ala | Met | Leu | Arg | Gln | Lys | Ala | Glu | Glu | Ser | Lys | Gln | Glu | Arg |      |
| 305 |     |     |     | 310 |     |     |     |     | 315 |     |     |     |     | 320 |     |      |
| tac | ctg | aag | tac | cag | agc | atg | aac | ctg | tac | gtc | aag | aac | ctg | tcc | gac | 1008 |
| Tyr | Leu | Lys | Tyr | Gln | Ser | Met | Asn | Leu | Tyr | Val | Lys | Asn | Leu | Ser | Asp |      |
|     |     |     |     | 325 |     |     |     |     | 330 |     |     |     |     | 335 |     |      |
| gag | gag | gtc | gac | gac | gac | gcc | ctg | cgt | gag | ctg | ttc | gcc | aac | tct | ggc | 1056 |
| Glu | Glu | Val | Asp | Asp | Asp | Ala | Leu | Arg | Glu | Leu | Phe | Ala | Asn | Ser | Gly |      |
|     |     |     | 340 |     |     |     |     | 345 |     |     |     |     | 350 |     |     |      |
| acc | atc | acc | tcg | tgc | aag | gtc | atg | aag | gac | ggc | agc | ggc | aag | tcc | aag | 1104 |
| Thr | Ile | Thr | Ser | Cys | Lys | Val | Met | Lys | Asp | Gly | Ser | Gly | Lys | Ser | Lys |      |
|     |     | 355 |     |     |     |     | 360 |     |     |     |     | 365 |     |     |     |      |
| ggc | ttc | ggc | ttc | gtg | tgc | ttc | acc | agc | cac | gac | gag | gcc | acc | cgg | ccg | 1152 |
| Gly | Phe | Gly | Phe | Val | Cys | Phe | Thr | Ser | His | Asp | Glu | Ala | Thr | Arg | Pro |      |
|     | 370 |     |     |     |     | 375 |     |     |     |     | 380 |     |     |     |     |      |
| ccc | gtg | acc | gag | atg | aac | ggc | aag | atg | gtc | aag | ggc | aag | ccc | ctg | tac | 1200 |
| Pro | Val | Thr | Glu | Met | Asn | Gly | Lys | Met | Val | Lys | Gly | Lys | Pro | Leu | Tyr |      |
| 385 |     |     |     |     | 390 |     |     |     |     | 395 |     |     |     |     | 400 |      |
| gtg | gcc | ctg | gcg | cag | cgc | aag | gac | gtg | cgc | cgt | gcc | acc | cag | ctg | gag | 1248 |
| Val | Ala | Leu | Ala | Gln | Arg | Lys | Asp | Val | Arg | Arg | Ala | Thr | Gln | Leu | Glu |      |
|     |     |     |     | 405 |     |     |     |     | 410 |     |     |     |     | 415 |     |      |
| gcc | aac | atg | cag | gcg | cgc | atg | taa | ggatcc |  |     |     |     |     |     |     | 1278 |
| Ala | Asn | Met | Gln | Ala | Arg | Met |     |     |     |     |     |     |     |     |     |      |
|     |     |     | 420 |     |     |     |     |     |     |     |     |     |     |     |     |      |